US011247054B2

(12) United States Patent
Levy et al.

(10) Patent No.: US 11,247,054 B2
(45) Date of Patent: Feb. 15, 2022

(54) NANOPARTICLES FOR USE FOR ENHANCING BRAIN PERFORMANCES OR FOR TREATING STRESS

(71) Applicant: NANOBIOTIX S.A., Paris (FR)

(72) Inventors: Laurent Levy, Paris (FR); Marie-Edith Meyre, Saint Mande (FR); Agnès Pottier, Paris (FR)

(73) Assignee: NANOBIOTIX S.A., Paris (FR)

(*) Notice: Subject to any disclaimer, the term of this patent is extended or adjusted under 35 U.S.C. 154(b) by 96 days.

(21) Appl. No.: 16/472,215

(22) PCT Filed: Dec. 19, 2017

(86) PCT No.: PCT/EP2017/083608
§ 371 (c)(1),
(2) Date: Jun. 21, 2019

(87) PCT Pub. No.: WO2018/114988
PCT Pub. Date: Jun. 28, 2018

(65) Prior Publication Data
US 2020/0086120 A1    Mar. 19, 2020

(30) Foreign Application Priority Data
Dec. 21, 2016  (EP) .................................. 16306752

(51) Int. Cl.
*A61N 1/36* (2006.01)
*A61K 45/06* (2006.01)
(Continued)

(52) U.S. Cl.
CPC .......... *A61N 1/36025* (2013.01); *A61K 45/06* (2013.01); *A61N 1/0456* (2013.01); *A61N 2/006* (2013.01); *B82Y 5/00* (2013.01)

(58) Field of Classification Search
CPC .. A61N 1/36025; A61N 1/0456; A61N 2/006; A61N 1/36014; A61K 45/06;
(Continued)

(56) References Cited

U.S. PATENT DOCUMENTS 10,588,987 B2    3/2020  Poul et al.
2004/0254419 A1* 12/2004  Wang ...................... A61L 31/16
                                                         600/8

(Continued)

FOREIGN PATENT DOCUMENTS

WO    WO 2006/126771    11/2006
WO    WO 2014/202723    12/2014
(Continued)

OTHER PUBLICATIONS

Guguru, R. et al. "Magnetoelectric 'spin' on stimulating the brain" *Nanomedicine*, 2015, pp. 2051-2061, vol. 10, No. 13.
(Continued)

*Primary Examiner* — Amanda K Hulbert
*Assistant Examiner* — Natasha Patel
(74) *Attorney, Agent, or Firm* — Saliwanchik, Lloyd & Eisenschenk

(57) ABSTRACT

The present invention relates to the medical field, in particular to the enhancement of brain performances and to the treatment of pathological stress. More specifically the present invention relates to a nanoparticle or nanoparticles' aggregate for use in enhancing brain performances or in prevention or treatment of pathological stress in a subject when the nanoparticle and/or nanoparticles' aggregate is exposed to an electric field, wherein the nanoparticle's or nanoparticles' aggregate's material is selected from a conductor material, a semiconductor material, an insulator material with a dielectric constant $\varepsilon_{ijk}$ equal to or above 200, and an insulator material with a dielectric constant $\varepsilon_{ijk}$ equal
(Continued)

Figure 1:
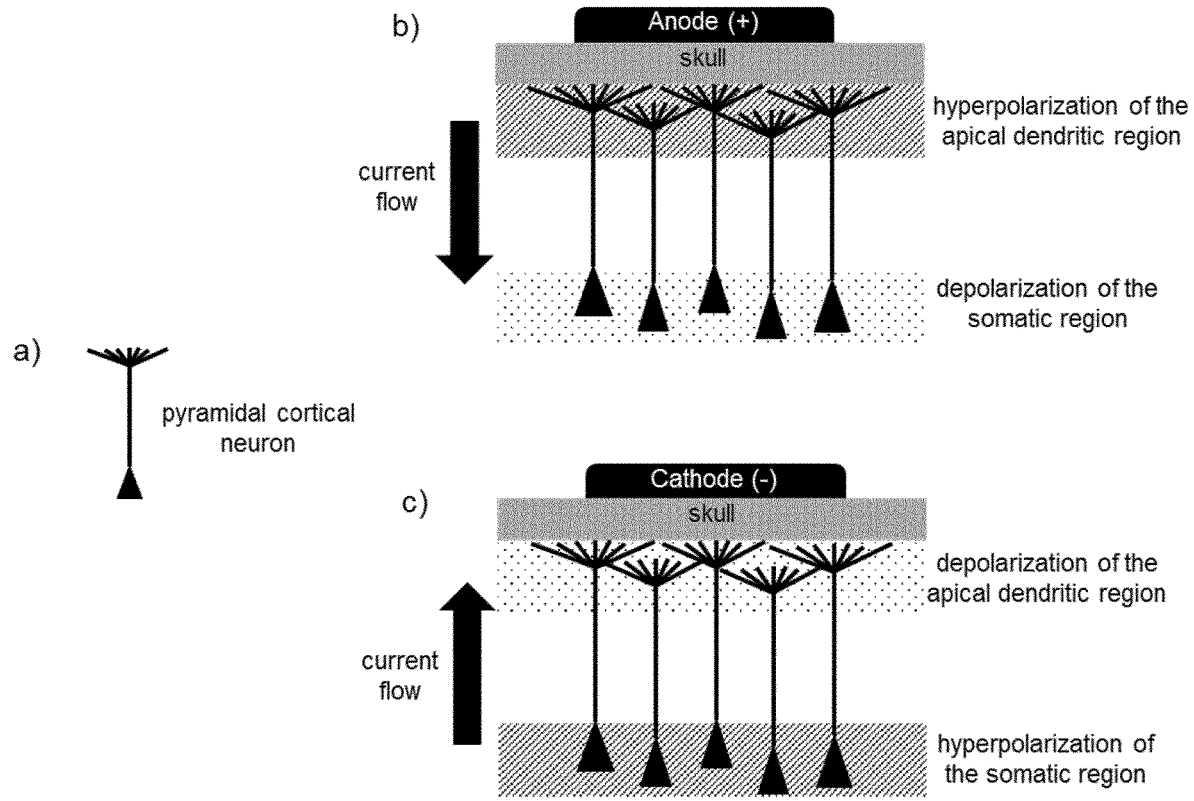

to or below 100. It further relates to compositions and kits comprising such nanoparticles and/or nanoparticles' aggregates as well as to uses thereof.

21 Claims, 8 Drawing Sheets

(51) Int. Cl.
*A61N 1/04* (2006.01)
*A61N 2/00* (2006.01)
*B82Y 5/00* (2011.01)

(58) Field of Classification Search
CPC ...... A61K 41/0052; A61K 41/00; B82Y 5/00; A61P 43/00
See application file for complete search history.

(56) References Cited

U.S. PATENT DOCUMENTS

| | | | |
|---|---|---|---|
| 2009/0326614 A1* | 12/2009 | El-Sayed | A61K 41/0052 607/88 |
| 2011/0275912 A1* | 11/2011 | Boyden | A61L 2/08 600/309 |
| 2012/0121712 A1* | 5/2012 | Ciofani | A61N 1/205 424/490 |
| 2012/0263793 A1* | 10/2012 | Vitaliano | G01N 21/658 424/490 |
| 2013/0023714 A1* | 1/2013 | Johnston | A61P 35/00 600/1 |
| 2013/0317279 A1 | 11/2013 | Khizroev et al. | |
| 2013/0320273 A1 | 12/2013 | Kotov et al. | |
| 2014/0323946 A1 | 10/2014 | Bourke, Jr. et al. | |
| 2015/0182756 A1* | 7/2015 | Peyman | A61K 31/7105 600/12 |
| 2019/0351057 A1 | 11/2019 | Pottier et al. | |
| 2019/0351231 A1 | 11/2019 | Meyre et al. | |

FOREIGN PATENT DOCUMENTS

| | | |
|---|---|---|
| WO | WO 2018/114945 | 6/2018 |
| WO | WO 2018/115023 | 6/2018 |

OTHER PUBLICATIONS

Borducchi, D. M. M. et al. "Transcranial Direct Current Stimulation Effects on Athletes' Cognitive Performance: An Exploratory Proof of Concept Trial" *Frontiers in Psychiatry*, Nov. 2016, pp. 1-5, vol. 7, Article 183.

Written Opinion in International Application No. PCT/EP2017/083608, dated Mar. 15, 2018, pp. 1-8.

Yong, J. ef al."Gold-Nanorod-Assisted Near-Infrared Stimulation of Primary Auditory Neurons" *Adv. Healthcare Mater.*, 2014, pp. 1862-1868, vol. 3, No. 11.

Paviolo, C. et al. "Laser exposure of gold nanorods can induce intracellular calcium transients" *J. Biophotonics.*, 2014, pp. 761-765, vol. 7, No. 10.

Shah, S. et al. "Hybrid upconversion nanomaterials for optogenetic neuronal control" *Nanoscale*, 2015, pp. 16571-16577, vol. 7, No. 40.

Chen, R. et al. "Wireless magnetothermal deep brain stimulation" *Science*, Mar. 12, 2015, pp. 1-7, vol. 347, No. 6229.

Ciofani, G. et al. "Enhancement of Neurite Outgrowth in Neuronal-Like Cells following Boron Nitride Nanotube-Mediated Stimulation" *ACS Nano*, 2010, pp. 6267-6277, vol. 4, No. 10.

Marino, A. et al. "Piezoelectric Nanoparticle-Assisted Wireless Neuronal Stimulation" *ACS Nano*, 2015, pp. 7678-7689, vol. 9, No. 7.

Written Opinion in International Application No. PCT/EP2017/083658, dated Mar. 16, 2018, pp. 1-10.

Written Opinion in International Application No. PCT/EP2017/083533, dated Apr. 16, 2018, pp. 1-7.

Claims as filed for U.S. Appl. No. 16/472,214, filed Jun. 21, 2019, pp. 1-3.

Claims as filed for U.S. Appl. No. 16/472,216, filed Jun. 21, 2019, pp. 1-4.

Colombo, E. et al. "Nanoparticles: A Challenging Vehicle for Neural Stimulation" *Frontiers in Neuroscience*, Mar. 23, 2016, pp. 1-7, vol. 10, Article 105.

\* cited by examiner

NANOPARTICLES FOR USE FOR ENHANCING BRAIN PERFORMANCES OR FOR TREATING STRESS

CROSS-REFERENCE TO RELATED APPLICATION

This application is the U.S. national stage application of International Patent Application No. PCT/EP2017/083608, filed Dec. 19, 2017.

The present invention relates to the medical field, in particular to the enhancement of brain performances and to the treatment of pathological stress. More specifically the present invention relates to a nanoparticle or nanoparticles' aggregate for use in enhancing brain performances or in prevention or treatment of pathological stress in a subject when the nanoparticle or nanoparticles' aggregate is exposed to an electric field/stimulus, wherein the nanoparticle's or nanoparticles' aggregate's material is selected from a conductor material, a semiconductor material, an insulator material with a dielectric constant $\varepsilon_{ijk}$ equal to or above 200, and an insulator material with a dielectric constant $\varepsilon_{ijk}$ equal to or below 100. It further relates to compositions and kits comprising such nanoparticles and/or nanoparticles' aggregates as well as to uses thereof.

BACKGROUND

With advancing comprehension of neuroscience, brain can be thought as an electric network, coding and transmitting information through its electric wires, neurons. Connectivity between neurons is simple and complex at the same time: simple because it lies on influx/efflux of ions inside neurons, which result in action potentials (or "spikes" of electric activity); complex because the brain network is composed of hundreds of billion neurons, which form nodes, hubs and modules that demonstrate coordinated interactions, at various spatial and temporal scales (Fornito et al., *Nature Reviews Neuroscience*, 2015, 16, 159-172: *The connectomics of brain disorders*). Neural communication depends on the anatomical components that connect individual neurons (structure) and on the process of transmitting information (function). Both aspects affect the overall performance of the nervous system. Neuronal interactions are traduced by oscillations of the brain electric activity pattern, which oscillations are measurable typically by electroencephalogram (EEG). Different frequency bands of oscillations are observed: delta, theta, alpha, beta, gamma (Ward et al., *Trends in Cognitive Sciences*, 2003, 7(12), 553-559: *Synchronous neural oscillations and cognitive processes*). Structurally, the most striking neuroanatomical feature of the brain is the abundant connectivity between neurons, which reflects the importance of neural communication. Synchronization of oscillations ("synchrony") between one brain area and another seems to constitute the last level of information coding [first level (neuron): action potentials; second level (neuronal network(s)): neuronal oscillations] by bringing spatio-temporal coordination (Engel et al., *Nature Reviews Neuroscience*, 2001, 2, 704-716: *Dynamic predictions: oscillations and synchrony in top-down processing*). Importantly, evidence is emerging that a delicately balanced pattern of synchronization and desynchronization in space and time is fundamental to the functional performance of the nervous system (Schnitzler et al., *Nature Reviews Neuroscience*, 2005, 6, 285-296: *Normal and pathological oscillatory communication in the brain*).

The development of specific skills, creativity or idea generation in certain individuals and not others is something very puzzling and which is still not explained. However, the study of certain diseases and of their symptoms may help understanding the functioning of "normal" and "abnormal" brains. For example, it has been observed that individuals with a neurodegenerative disease like frontotemporal dementia develop drawing and painting skills with the advancement of their disease (Miller et al., *Neurology*, 1998, 978-982: *Emergence of artistic talent in frontotemporal dementia*). Several publications demonstrate that the propensity to suffer from a neurological disease, like bipolar syndrome, schizophrenia or autism, is higher for people (and their first-degree relatives) working in a creative domain (engineering, literature, painting), than for "non-creative people" (Andreasen N. C., *American Journal of Psychiatry*, 1987, 144(10), 1288-1292: *Creativity and mental illness: prevalence rates in writers and their first-degree relatives*; Baron-Cohen et al., *Autism*, 1997, 101-109: *Is there a link between engineering and autism*; Sussman et al., *Stanford Journal of Neuroscience*, 2007, 1(1), 21-24: *Mental illness and creativity: a neurological view of the "tortured artist"*). Several models have been elaborated to describe the process of creation and idea generation: the hemispheric model, which suggests that the non-dominant hemisphere is specialized for creative activity, or more recently the frontotemporal model, which suggests that changes in the temporal lobe may increase idea generation whereas changes in the frontal lobe may decrease it (Flaherty et al., *J Comp Neurol*, 2005, 493(1), 147-153: *Frontotemporal and dopaminergic control of idea generation and creative drive*). Indeed, certain savants can perform esoteric numerical calculations while being deficient in elementary arithmetic (Snyder et al., *Proceedings of the Royal Society of London B*, 1999, 266, 587-592: *Is integer arithmetic fundamental to mental processing?: the mind's secret arithmetic*). Interestingly, there is evidence that such unusual ability is related with left (dominant) hemisphere inhibition together with right (non-dominant) hemisphere facilitation (Treffert D. A., *Philosophical Transactions of the Royal Society B*, 2009, 364, 1351-1357: *The savant syndrome: an extraordinary condition. A synopsis: past, present, future*).

Thus, brain is a dynamic system, where specific states of cerebral functioning derive from complex excitatory and inhibitory interactions between neuronal populations. Then, an "abnormal" state reflects an imbalance between complex excitatory and inhibitory interactions between neuronal populations (Kapur et al., *Brain*, 1996, 119, 1775-1790: *Paradoxical functional facilitation in brain-behaviour research, a critical review*).

Nowadays, modulation of the electric activity pattern of neurons (neuromodulation) may be induced through electrical stimulations. The current techniques to produce an electric stimulus into the brain utilize either a direct electric stimulation or the induction of an electric field through the application of an electric current through a magnetic coil.

Transcranial Direct Current Stimulation (tDCS) has already been used to test the impact of electrical stimulation on brain performances and physical skills. Briefly, tDCS consists of the application of a continuous weak current on skull surface, through sponge electrodes on two different brain areas, one stimulated by an anode, the other stimulated by a cathode. Several trials have shown that by applying electrodes on the skull surface and a current of less than 2 mA for less than 30 min, for people submitted to different tasks like mathematical learning, working memory, language learning or motor skill acquisition, an improvement in the performance of this task was observed when compared to sham stimulation (Filmer et al., *Trends in Neurosciences*, 2014, 37(12), 742-753: *Applications of transcranial direct current stimulation for understanding brain function*). A team from the Air Force Research Laboratory of the U.S. Department of Defense has recently demonstrated that applying anodal tDCS to military operators, at 2 mA during 30 min to the left dorsolateral prefrontal cortex (associated with sustained attention, working memory, decision making, planning and reasoning) significantly enhanced the multitasking capability of participants (Nelson et al., *Front. Hum. Neurosci.*, 2016, 10:589: *The effects of transcranial direct current stimulation on multitasking throughput capacity*).

Transcranial direct current stimulation has also been shown to produce beneficial neural effects resulting in improvements in motor behavior, notably physical capacities rehabilitation in the case of stroke (Madhavan et al., *Frontiers in Psychiatry*, 2012, 3(66), 1-9: *Enhancing motor skill learning with transcranial direct current stimulation—a concise review with applications to stroke*). In healthy people, electrical stimulation is envisaged as a mean to enhance, increase or upgrade physical performances/capacities (Banissy et al., *Frontiers in Human Neuroscience*, 2013, 7(129), 1-3: *Transcranial direct current stimulation in sports training: potential approaches*).

Electrical stimulation of brain is an interesting method to enhance brain performances/capacities. Recently, non-invasive neural stimulation techniques have been envisaged, such as the use of light or ultrasound to directly stimulate neurons.

Interestingly, nanomaterials with unique properties have been explored as mediator to convert a wirelessly transmitted primary stimulus to a localized secondary stimulus, primarily electric field or heat, at the nanomaterial-neuron interface (Wang Y. & Guo L. *Nanomaterial-enabled neural stimulation. Frontiers in Neuroscience.* 2016; vol. 10, Article 69). Thus, opto-electric transduction has been shown using quantum dots, opto-thermal transduction using gold nanomaterials, magneto-electric transduction using magneto-electric nanoparticles, magneto-thermal transduction using superparamagnetic nanoparticles and acousto-electric transduction using piezoelectric nanomaterials. For instance, magneto-electric (ME) nanoparticles are composite nanoparticles exhibiting piezoelectric and magnetostrictive properties. Concretely, the ME effect allowed for example by $CoFe_2O_4$—$BaTiO_3$ nanoparticles results from the combined actions of two distinct materials, i.e. a magnetostrictive ($CoFe_2O_4$) material and a piezoelectric ($BaTiO_3$) material. More precisely, when $CoFe_2O_4$—$BaTiO_3$ nanoparticles are exposed to a magnetic field: first, the magnetostrictive material changes its length (volume), thereby causing a local stress, second, the piezoelectric material produces an electric polarization (a charge) as a reaction to this local stress. None of the magnetostrictive material or of the piezoelectric material is capable of generating by itself either a ME effect or an electric polarization when exposed to a magnetic field, as explained by Grössinger R. et al. (Grössinger R. et al., *Journal of Magnetism and Magnetic Materials*, 2008, 320, 1972-1977: *The physics of magnetoelectric composites*).

The present invention deals with nanoparticles and/or nanoparticles' aggregates (aggregates of nanoparticles) for use in/for enhancing, increasing or improving brain performances/capacities or for preventing or treating/for use in prevention or treatment of pathological stress or at least one symptom thereof, when the nanoparticle or nanoparticles' aggregate is exposed to an electric field/stimulus. The electric field is typically applied through transcranial electric stimulation (TES) or transcranial magnetic stimulation (TMS).

The nanoparticles or nanoparticles' aggregates enhance the excitatory and/or inhibitory effect of the applied electric field on neuronal network(s) in one brain area and/or another, narrow the spatial resolution (focality) and increase the depth of penetration of the electric field, while using standard electrical stimulation techniques.

Moreover, the nanoparticles or aggregates of nanoparticles of the present invention allow a decrease of the applied current, voltage, pulse width and/or frequency and therefore reduce the known potential toxicity related to the applied/induced electrical current.

BRIEF DESCRIPTION

Herein advantageously described for the first time is a nanoparticle or nanoparticles' aggregate for use in/for enhancing, increasing, or improving brain performances/capacities or for preventing or treating/for use in prevention or treatment of pathological stress or at least one symptom thereof in a subject when the nanoparticle or nanoparticles' aggregate is exposed to an electric field/stimulus. The nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

Also herein described is the use of a nanoparticle or nanoparticles' aggregate for preparing a composition for enhancing, increasing, or improving brain performances/capacities or for preventing or treating pathological stress or at least one symptom thereof in a subject in need thereof.

Also herein described is a composition for use in/for enhancing brain performances or for preventing or treating/for use in prevention or treatment of pathological stress or at least one symptom thereof in a subject exposed to an electric field/stimulus, wherein the composition comprises, or consists of, nanoparticles and/or nanoparticles' aggregates and a pharmaceutically acceptable support, and wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

Further herein described is a kit comprising at least two distinct nanoparticles and/or nanoparticles' aggregates, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100, and uses thereof typically in enhancing brain performances or in a method for enhancing brain performances, or in prevention or treatment of pathological stress or at least one symptom thereof in a subject.

DETAILED DESCRIPTION

The human nervous system is estimated to consist of roughly 80-120 billion nerve cells (Herculano-Houzel S. Frontier in *Human Neuroscience* (2009), 3(31): 1-11: *The human brain in numbers: a linearly scaled-up primate brain*). The defining characteristic of a neuron (or nerve cell) is its ability to transmit electrical signals in the form of action potentials.

The neuron/nerve cell constitutes the elementary node of the brain. The structure of a neuron/nerve cell consists of: the "soma" or "cell body", which contains the nucleus and can be prolonged by dendrites, the "axon", which transmits the electrical signal, and the axon terminal, which consists of the synaptic terminals.

Nerve cells can communicate with each other in a highly-structured manner forming neuronal networks. Neuron communicates via synaptic connections. Within neuron, nanocircuits constitute the underlying biochemical machinery for mediating key neuronal properties such as learning and memory and the genesis of neuronal rhythmicity.

A microcircuit can be formed with just only a few interconnected neurons and can perform sophisticated tasks such as mediate reflexes, process sensory information, initiation of locomotion, and learning and memory mediation. A macrocircuit is a more complex network which consists of multiple imbedded microcircuits. Macrocircuits mediate higher brain functions such as object recognition and cognition. So, multiple levels of networks occupy the nervous system.

Neural Network Excitability

Neurons send messages electrochemically (i.e. chemicals/ions cause an electrical signal). The important ions in the nervous system are sodium and potassium, calcium and chloride. When a neuron is not sending a signal, it is "at rest." When a neuron is at rest, the inside of the neuron is negative relative to the outside. Although the concentrations of the different ions attempt to balance out on both sides of the membrane, they cannot because the cell membrane allows only some ions to pass through channels (ion channels). In addition to these selective ion channels, there is a pump that uses energy to move three sodium ions out of the neuron for every two potassium ions it puts in. Finally, when all these forces balance out, and the difference in the voltage between the inside and outside of the neuron is measured, the resting membrane potential (also "resting potential") of a neuron is about −70 mV. This means that the inside of the neuron is 70 mV less than the outside. At rest, there are relatively more sodium ions outside the neuron and more potassium ions inside that neuron. An action potential (also identified as "spike" or "impulse") occurs when a neuron sends information down an axon, away from the cell body. This means that some event (a stimulus) causes the resting potential to move toward 0 mV. When the depolarization reaches about −55 mV the neuron fires an action potential. If the depolarization does not reach this critical threshold level, then no action potential fires (on/off mechanism). Also, when the threshold level is reached, an action potential of fixed amplitude always fires. Therefore, either the depolarization does not reach the threshold or a full action potential is generated.

A great variability is found in the velocity of the propagation of action potentials. In fact, the propagation velocity of the action potentials in nerves can vary from 100 meters per second to less than a tenth of a meter per second. Whereas the time constant is an index of how rapidly a membrane will respond to a stimulus in time, the space constant (also length constant) is an index of how well an electric potential will spread along an axon as a function of distance.

Connectivity within and Between Neuronal Networks

There are three connectivity network types that are used to investigate communication within and across the brain. Structural connectivity is based on the detection of the fiber tracks that physically connect the regions of the brain. These are the anatomical network maps that indicate possible pathways that the signals can travel on in the brain. Functional connectivity identifies activity in brain regions that have similar frequency, phase and/or amplitude of correlated activity. Effective connectivity uses the functional connectivity information and goes one step further in determining the direct or indirect influence that one neural system may have over another, more specifically the direction of the dynamic information flow in the brain (Bowyer et al., *Neuropsychiatric Electrophysiology*, 2016, 2(1), 1-12: *Coherence a measure of the brain networks: past and present*). The synchronized activity within a neuronal network can be detected by magnetoencephalogram (MEG), electroencephalogram (EEG), Functional Magnetic Resonance Imaging (FMRI) or Positron Emission Tomography (PET), then image using network connectivity analysis. MEG (Magnetoencephalogram) or EEG (Electroencephalogram) are preferred because they have high temporal resolution to resolve the dynamic flow of information. Connectivity analysis of the brain is performed to map out the communication networks needed for the brain to function. Specific regions in the brain are specialized for processing certain types of information. Imaging techniques have revealed that these regions are connected and communicate with other specialized regions across networks in the brain. "Coherence" (Bowyer et al.) is a mathematical technique that quantifies the frequency and amplitude of the synchronicity (the state of being in synchrony or of being synchronized) of neuronal patterns of oscillating brain activity. Detection of the synchronous activation of neurons can be used to determine the wellbeing or integrity of the functional connectivity in the human brain. Overlaying the functional connectivity maps onto the structural connectivity images and the using direction of information flow derived from effective connectivity provides an all-inclusive understanding of how the brain functions.

The intact brain expresses complex patterns of synchronous activity, associated with different 'states' of the organism, from slow delta rhythm (0.5-4 Hz), through theta (4-8 Hz), alpha (8-12 Hz), beta (15-30 Hz) and gamma (30-70 Hz) oscillations. Interestingly, the dissociated culture of cortical structures offers a convenient system for the examination of the rules that govern the emergence, generation and spread of network firing (spikes) and bursting (clusters of spikes) in populations of densely interconnected neurons. Network activity can be recorded for extended periods of time in a non-invasive manner and with finite time resolution using multielectrodes arrays. The 2-dimensional dissociated culture can be used as a viable test system for studying rules that govern the formation and maintenance of network activity in the brain, allowing the testing of hypothesis that cannot be addressed in the intact brain (Cohen E. et al., *Brain Research*, 2008, 1235, 21-30: *Determinants of spontaneous activity in networks of cultured hippocampus*).

Human mental abilities or brain performances, such as intelligence, are particularly complex. Understanding these abilities in mechanistic terms has the potential to facilitate their enhancement. Studies using encephalograms and event-related potentials indicate that the speed and reliability of neural transmission are related to higher performances, typically to higher intelligence. Early neuroimaging studies using PET found that intelligence correlated negatively with cerebral glucose metabolism during mental activity, leading to the formulation of a 'neural efficiency' hypothesis. According to this hypothesis, more intelligent individuals expend fewer neuronal resources to perform at a given level. Intelligence in the sense of reasoning and novel problem-solving ability is consistently linked to the integrity, structure and function of the lateral prefrontal cortex, and possibly to that of other areas. Outstanding questions about the neural bases of intelligence include among others the relationships between psychometric intelligence (i.e. intelligence as measured by an IQ-type test, typically assessing the accuracy of a response (and not the speed)) and (i) functional connectivity between components of working memory networks as indicated by electroencephalogram-based studies and (ii) neural plasticity (i.e. used to refer to those processes that involve major connectional changes of the nervous system in response to experience and that are observed to cease to operate at maturity in human). The development of neural connections was reported to be consistent with the development of intelligence (Gray J. R. et al., *Nature Review Neuroscience*, 2004, 5, 471-482: *Neurobiology of intelligence: science and ethics*; Garlick D., *Psychological Review*, 2002, 109(1), 116-136: *Understanding the nature of general factor of intelligence: the role of individual difference in neural plasticity as an explanatory mechanism*).

Communication among neurons is indeed essential for higher brain functions such as perception, memory and movement (Massobrio P et al. *Neural Plasticity*, 2015, Article ID 196195, *In vitro studies of neuronal networks and synaptic plasticity in invertebrates and in mammals using multi electrode arrays*). While the formation and development of connections is assumed to be crucial in the process of learning, their conservation appears to be essential for memory. Synaptic plasticity has long been implicated in cognitive processes such as learning and memory. Synaptic plasticity at the network level provides a distributed mechanism to convert and store temporal information into spatially distributed patterns of synaptic modifications. Each time something is learned, the network develops a new connectivity and incorporates the newly learned facts. It is known that electrical stimulation can efficiently induce modifications in the network synchronization and in particular affects the network bursting properties by increasing both firing and bursting rates. Moreover, after this kind of spontaneous activity-tailored stimulation, the strongest connections respond by further increasing their strength relative to other connections within the network. This mechanism likely preserves connections that are more informative and relevant to the overall network activity. Chiappalone et al. (*European Journal of Neuroscience*, 2008, 28, 221-237: *Network plasticity in cultured cortical assemblies*) found that application of a high frequency tetanic stimulation with or without a 0.2 Hz low frequency in phase or 1 Hz iso-frequential co-activation is able to induce a global network synaptic potentiation. The network response clearly increased because of synaptic potentiation which can be appreciated by looking at the increase in the number of effective connections of the network (Poli D. et al. *Frontiers in Neural Circuits.*, 2015, 9, article 57: *Functional connectivity in in vitro neuronal assemblies*). Le Feber et al. (*PLoS ONE*, 2010, 5(1), e88871: *The effect of slow electrical stimuli to achieve learning in cultured networks of rat cortical neurons*) applied to cortical cultures in the mature stage of development biphasic current pulses at a frequency of 0.2-0.33 Hz to investigate possible modifications of the network functional connectivity, and consequently synaptic plasticity. They found that electrical stimulation affected the number of functional links (connections), as well as the average magnitude of changes.

Effective connections between neurons may be detected using for example multielectrodes arrays on dissociated neural cultures as presented in Chiappalone et al. (*European Journal of Neuroscience*, 2008, 28, 221-237: *Network plasticity in cultured cortical assemblies*) or imaging methods well known by the skilled person such as electron-based imaging methods which provide structural information about synaptic connectivity, typically electron microscopy (EM), for example serial block-face electron microscopy (SBFEM), serial section scanning electron microscopy (SS-SEM), automated transmission EM (ATEM), etc.; photon-based imaging methods, for example "Brainbow" (Lichtman J W et al., *Curr Opin Neurobiol*, 2008, 22, 144-153: *Ome sweet ome: what can the genome tell us about the connectome?*; Cai D., et al., *Nat Methods*, 2013, 10(6), 540-547: *Improved tools for the Brainbow toolbox*), "array tomography" (AT) (Micheva K D., et al., 2007, *Neuron*, 55, 25-36: *Array tomography: a new tool for imaging the molecular architecture and ultrastructure of neural circuits*; Micheva K D., et al., 2010, *Neuron*, 68, 639-653: *Single-synapse analysis of a diverse synapse population: proteomic imaging methods and markers*), GFP reconstitution across synaptic partners ("GRASP"), in particular mammalian GRASP "mGRASP" (Kim J, et al., 2012, *Nat Methods*, 9(1), 96-102: *mGRASP enables mapping mammalian synaptic connectivity with light microscopy*; Feng L, et al., 2012, *Bioinformatics*, 28, i25-i31: *Improved synapse detection for mGRASP-assisted brain connectivity*), Trans-synaptic tracing by rabies virus (Osakada F, et al., 2011, *Neuron*, 71, 617-631: *New rabies virus variants for monitoring and manipulating activity and gene expression in defined neural circuits*; Wickersham I R, et al., 2007, *Nat Methods*, 4(1), 47-49: *Retrograde neuronal tracing with a deletion-mutant rabies virus*; Wickersham I R, et al., 2007, *Neuron*, 53(5), 639-647: *Monosynaptic restriction of transsynaptic tracing from single, genetically targeted neurons*), fluorescent selective plane illumination microscopy (fSPIM) (Tomer R, et al., 2012 *Nat methods*, 9, 755-763: *Quantitative high-speed imaging of entire developing embryos with simultaneous Multiview light-sheet microscopy*; York A G, et al., 2012, *Nat Methods*, 9(7), 749-754: *Resolution doubling in live, multicellular organisms via multifocal structured illumination microscopy*) preferably in combination with a clearing method such as "CLARITY" (Chung K, et al., 2013, *Nature*, 497 (7449), 332-337: *Structural and molecular interrogation of intact biological systems*); as well as optogenetic methods such as channel-rhodopsin and/or two-photon microscopic calcium imaging methods which allow the mapping of the spatial distribution of synaptic connections together with measures of synaptic strength (Petreanu L, et al., 2007, *Nat Neurosci*, 10, 663-668: *Channelrhodopsin-2-assisted circuit mapping of long-range callosal projections*; Wang H, et al., 2007, *Proc Natl Acad Sci USA*, 104, 8143-8148: *High-speed mapping of synaptic connectivity using photostimulation in channelrhodopsin-2 transgenic mice*) as well as the detection of active synapses innervated by different inputs (Little J P, et al., 2012, *J Neurosci: Off J Soc Neurosci*, 32(37), 12808-12819: *Subcellular synaptic connectivity of layer 2 pyramidal neurons in the medial prefrontal cortex*; MacAskill A F, et al., 2012, *Nat Neurosci*, 15(12), 1624-1626: *Subcellular connectivity underlies pathway-specific signaling in the nucleus accumbens*); or any combinations of these different methods (Yook C. et al., *Cellular and Molecular Life Sciences*, 2013, 70, 4747-4757: *Mapping mammalian synaptic connectivity*).

Network activity changes induce changes in the density of the 2-amino-3-(5-methyl-3-oxo-1, 2-oxazol-4-yl) propanoic acid (AMPA) glutamate receptor subunits that are present on the spines found in excitatory synapses. Such perturbations can influence action potential probability and the resulting firing rate within a network of neurons. These types of synaptic modulations have been observed in association with learning and memory and are thought to underlie the neural substrate of memory known as Long Term Potentiation (LTP). Niedringhaus M. et al. (*PLoS ONE*, 2013, 8(3), e57144: *Synaptic Potentiation Facilitates Memory-like Attractor: Dynamics in Cultured In Vitro Hippocampal Networks*) described the temporal network activity that arises when pharmacological agents forskolin (50 mM) and rolipram (100 nM) were introduced in cultured hippocampal neurons in order to induce chemical Long Term Potentiation (LTP). Authors observed a large increase in spiking and bursting activities after chemical LTP. Moreover, after chemical LTP, the bursts appear to cluster into tightly organized episodes of shortened duration and higher frequency. There was a uniform decrease in the coefficient of variation of inter-spikes intervals across all electrodes that experienced the chemical LTP treatment. Therefore, their results suggested that the molecular modulations at the synapse, stimulated by the increased potentiation, resulted in the restructuring of the bursts as they formed tightly compacted episodes of persistent activity. Bursts are important during development as they facilitate normal functioning in developing neurons that in turn helps to create viable connections. These combined results demonstrated that synaptic potentiation was responsible for the restructuration of the burst profile. These restructured bursts facilitate information storage within the network.

Structure of the Cerebral Cortex

There are two broad classes of cortical neurons: "inhibitory neurons" or "interneurons", which make only short-range, local connections; and "excitatory neurons" or "projection neurons" or "pyramidal neurons", which extend axons to distant intracortical, subcortical and subcerebral targets. "Inhibitory neurons" or "interneurons" constitute a minority (20%) of the cortical neurons; the majority is contained in "pyramidal neurons" (Shipp S., *Current Biology*, 2007, 17(12), R443-449: *Structure and function of the cerebral cortex*). Projection neurons are glutamatergic neurons that transmit information between different regions of the neocortex and to other regions of the brain (Bikson et al., *J Physiol*, 2004, 557(1), 175-190: *Effects of uniform extracellular DC electric fields on excitability in rat hippocampal slices in vitro*). Projection neurons or pyramidal neurons are named for their prominent apical dendrite, which typically points superficially, providing them a pyramidal morphology. Customarily, a neuron "belongs" to the layer in which its cell body (or "soma") is sited—even if the apical and basal dendrites, between them, span several more layers, picking up a broader range of signals (Shipp S., *Current Biology*, 2007, 17(12), R443-449: *Structure and function of the cerebral cortex*).

The grey matter of the cerebral cortex is a convoluted, layered sheet of tissue, 2-3 millimeters thick in man but with a surface area of several hundred square centimeters (Shipp S., *Current Biology*, 2007, 17(12), R443-449: *Structure and function of the cerebral cortex*). Six major layers are recognized in the cerebral cortex:

Layer I, the molecular layer, contains few scattered neurons and consists mainly of extensions of apical dendritic tufts of pyramidal neurons and horizontally oriented axons, as well as glial cells;

Layer II, the external granular layer, contains predominantly small and medium-size pyramidal neurons and numerous stellate neurons;

Layer III, the external pyramidal layer, contains predominantly small and medium-size pyramidal neurons, as well as non-pyramidal neurons with vertically oriented intracortical axons;

Layer IV, the internal granular layer, contains different types of stellate and pyramidal neurons;

Layer V, the internal pyramidal layer, contains large pyramidal neurons which give rise to axons leaving the cortex and running down to subcortical structures (such as the basal ganglia). In the primary motor cortex of the frontal lobe, layer V contains cells whose axons travel through the internal capsule, the brain stem and the spinal cord forming the corticospinal tract, which is the main pathway for voluntary motor control; and Layer VI, the polymorphic or multiform layer, contains few large pyramidal neurons and many small spindle-like pyramidal and multiform neurons; layer VI send efferent fibers to the thalamus, establishing a very precise reciprocal interconnection between the cortex and the thalamus.

These layers are differently developed in various regions of the cerebral cortex, e.g. pyramidal layers are more developed in the motor centers and granular layers in sensory centers of the cerebral cortex.

Modulation of Cortical Excitability with Electric Stimulation

Transcranial Direct Current Stimulation (tDCS) is an electric stimulation technique of the brain cortex involving electrodes (one anode and one cathode) placed on the skull surface. As such, tDCS induces a modulation of the cortical excitability and plastic changes in neuronal network(s).

The current used in tDCS modulates spontaneous neuronal activity in a polarity-dependent fashion. Surface anodal stimulation will typically produce inward current flow at the cortex, which is expected due to somatic depolarization of pyramidal cortical neurons and apical dendrite hyperpolarization, while surface cathodal stimulation will typically produce outward current flow at the cortex and is expected to result in somatic hyperpolarization of pyramidal cortical neurons and apical dendrite depolarization (Kadosh R C, "*The stimulated brain*", 2014, edited by Elsevier) (cf. FIG. 1).

Neuron polarizability can also depend on the direction of the applied electric field compared to the axis of the neuron (Bikson et al., *J Physiol*, 2004, 557, 1, 175-190: *Effects of uniform extracellular DC electric fields on excitability in rat hippocampal slices in vitro*). Different electrode configurations exist, resulting in different types of stimulation and current flow (cf. FIG. 2). The brain area stimulated by the anode constitutes an area where neuronal activity is excited/facilitated, whereas the brain area stimulated by the cathode constitutes an area where neuronal activity is inhibited (Kadosh R C, "*The stimulated brain*", 2014, edited by Elsevier) (cf. FIG. 3).

Herein advantageously described for the first time is a nanoparticle or nanoparticles' aggregate for use in/for enhancing, increasing or improving brain performances/capacities or for preventing or treating/for use in prevention or treatment of pathological stress or at least one symptom thereof when the nanoparticle or nanoparticles' aggregate is exposed to an electric field/stimulus. The nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

In a typical aspect, the nanoparticle or nanoparticles' aggregate herein described is for use in/for enhancing physical performances, or in/for enhancing cognitive performances, i.e. learning, memorizing, sense perception, attention and/or decision making of a subject.

For example, most of studies over the last century find that no participants can solve the nine-dot problem, a problem which consists of connecting nine dots with four straight lines, drawn without lifting pen from paper or retracing a line. Chi et al. show that applying tDCS (direct current of 1.6 mA with a specific configuration of electrodes) during 10 min allows more than 40% of the participants (total of 22 participants) to solve the problem (Chi et al., *Neuroscience Letters*, 2012, 515, 121-124: *Brain stimulation enables the solution of an inherently difficult problem*). Another experiment with another type of problem, the "matchstick arithmetic" (participants were asked to correct a false arithmetic statement, presented in Roman numerals constructed from matchsticks, by moving one stick from one position to another position without adding or discarding a stick), demonstrates the same facilitation of problem solving thanks to electric stimulation with tDCS (Chi et al., *PLOS One*, 2011, 6(2), e16655: *Facilitate insight by non-invasive brain stimulation*).

Enhancement of motor function, which then results in enhancement of physical performances, is one exciting application for improving brain functionality. By stimulating specific areas of the motor cortex, increase of fine motor skills as well as modulating gross motor properties such as fatigue and explosiveness has been demonstrated in human subjects. Vines et al. and Cuypers et al. show improved motor skills and motor learning using tDCS and a finger tapping task. In the Vines' study, participants had to match numbers on a screen with keys on a keyboard, with each key assigned to a particular finger. The participants who received bihemispheric stimulation were faster and more accurate when completing the task, producing both more responses and a greater fraction of correct responses, compared to participants who received unihemispheric or sham stimulation (Vines et al., *BMC Neuroscience*, 2008, 9, 103, 1-7: *Dual-hemisphere tDCS facilitates greater improvements for healthy subjects' non-dominant hand compared to uni-hemisphere stimulation*). Cuypers et al. used a similar protocol to test how increased stimulation (1.5 mA vs 1 mA) affects motor learning. Here, researchers replicated the findings of Vines et al. while showing that increased stimulation yielded a further increase in speed and accuracy when completing the task (Cuypers et al., *PLOS One*, 2013, 8(6), e67344: *Is motor learning mediated by tDCS intensity?*).

Thus, electrical stimulation is herein described as a mean to enhance, increase or upgrade physical performances/capacities, more peculiarly in sports training (Banissy et al., *Frontiers in Human Neuroscience*, 2013, 7(129), 1-3: *Transcranial direct current stimulation in sports training: potential approaches*).

Electrical Stimulation

In the context of the invention, the electric field is preferably applied through transcranial electric stimulation or transcranial magnetic stimulation.

When the cerebral cortex is to be reached, the electrical stimulation is performed on the surface (penetration depth of the electric field is usually equal to or below 2 cm under the skin surface; with specific technique—specific coils for Transcranial Magnetic Stimulation—the electric field can reach 5 cm depth). Techniques providing such an electric field include typically Transcranial Magnetic Stimulation (TMS), repetitive Transcranial Magnetic Stimulation (rTMS), transcranial Direct Current Stimulation (tDCS), High-definition transcranial Direct Current Stimulation (HD-tDCS), Transcranial Electrical Stimulation (TES), transcranial Alternating Current Stimulation (tACS), transcranial Pulsed Current Stimulation (tPCS) and transcranial Random Noise Stimulation (tRNS; alternate current along with random amplitude and frequency). The most widely used in clinical trials, and preferred in the context of the invention, are TMS and tDCS.

Transcranial Magnetic Stimulation (TMS)

Transcranial Magnetic Stimulation (TMS) is a non-invasive technique that is used or investigated for numerous research and therapeutic applications, including the study of normal and pathological brain functions and the treatment of neural disorders, and which is usable in the context of the invention. TMS uses brief, intense pulses of electric current delivered to a coil placed on the subject's head to generate an electric field in the brain via electromagnetic induction. The induced electric field modulates the neural transmembrane potentials and, thereby, neural activity. The locus of activation in the brain is approximately in the area where the induced electrical field is maximal; this location, in turn, depends on the stimulating coil's geometry and placement. Two electric field spatial features of interest are depth of penetration and focality, which both depend on the coil geometry and are easily determinable by the skilled person.

Transcranial Direct Current Stimulation (tDCS)

Transcranial Direct Current Stimulation (tDCS) is a non-invasive technique, usable in the context of the invention, where brain stimulation is performed thanks to a direct current, leading to changes in the cortical excitability. tDCS uses a low-intensity (0.5-2 mA) constant current which is applied directly to the head via two electrodes (anode/cathode) of typically 20-35 $cm^2$. One electrode (reference electrode) can be placed over the forehead (above the supraorbital ridge) and the other (active electrode) can be placed over the contralateral hemisphere, commonly over the motor cortex (M1) or the dorsolateral prefrontal cortex, depending on the design. The duration of the stimulation most often ranges between 20 and 40 minutes. A portion of current penetrates the brain, producing a peak electric field of approximately 0.3 V/m per 1 mA applied. The sustained electric field produced during tDCS modifies the transmembrane neuronal potential and can influence the level of excitability and the responsiveness to synaptic input, and modulates the firing rate of individual neurons. Increased excitability occurs with anodal stimulation, whereas decreased excitability typically occurs with cathodal stimulation.

Nanoparticles

Herein described is a nanoparticle or aggregate of nanoparticles for use according to the invention in/for enhancing brain performances or for preventing or treating/for use in prevention or treatment of pathological stress or at least one symptom thereof in a subject when said nanoparticle or aggregate of nanoparticles is exposed to an electric field, wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

Composition of Nanoparticles

Nanoparticle Prepared from a Conductor Material

The nanoparticle prepared from a conductor material is an organic nanoparticle or an inorganic nanoparticle.

Inorganic nanoparticle prepared from a conductor material is typically prepared with a metallic element having a standard reduction potential E° value equal to or above about 0.01, typically when measured at 25° C. and at a pressure of 1 atm in respect to the standard hydrogen electrode (see Table 2 "reduction reactions having E° values more positive than that of the standard hydrogen electrode", 8-25, Handbook of chemistry and physics; David R. Lide; 88$^{th}$ Edition), more preferably equal to or above about 0.1, 0.2, 0.4, or 0.5. Typical metallic elements used to prepare the nanoparticles may be selected from Tl, Po, Ag, Pd, Ir, Pt, Au, and a mixture thereof. Preferably, the metallic element usable as conductor material to prepare the nanoparticles is selected from Ir, Pd, Pt, Au, and a mixture thereof.

Organic nanoparticle prepared from a conductor material is typically prepared with an organic material having contiguous sp2 hybridized carbon centers in its structure (i.e. carbon double bond or aromatic cycles comprising heteroatoms, typically N or S, within the aromatic cycle or outside the aromatic cycle). Preferred organic materials are selected from polyaniline, polypyrrole, polyacetylene, polythiophene, polycarbazole, polypyrene, poly(3,4-ethylenedioxythiophene) and/or poly(3,4-ethylenedioxythiophene) polystyrene sulfonate.

Nanoparticle Prepared from a Semiconductor Material

The nanoparticle prepared from a semiconductor material is typically an inorganic nanoparticle. Inorganic nanoparticles are typically prepared with a semiconductor material presenting a relatively small energy band gap (Eg) between its valence and conduction bands. Typically, the semiconductor material has a band gap Eg below 3.0 eV, typically when measured at room temperature (25° C.). In a particular aspect, the material is an intrinsic semiconductor material or an extrinsic semiconductor material as further herein described below.

Intrinsic semiconductor materials typically consist of an element from group IV A of the Mendeleev's periodic table, such as Silicon (Si) or Germanium (Ge), in a mixed composition of elements from groups III and V of the Mendeleev's periodic table, such as AlSb, AlN, GaP, GaN, InP, InN, etc., or in a mixed composition of elements from groups II and VI of the Mendeleev's periodic table, such as ZnSe, ZnTe, CdTe, etc.

Extrinsic semiconductor materials typically comprise, or consist of, an intrinsic semiconductor prepared with a high degree of chemical purity, wherein the intrinsic semiconductor material comprises a dopant. In a particular aspect, when the nanoparticle's or nanoparticles' aggregate's extrinsic semiconductor material consists of an element from group IVA of the Mendeleev's periodic table, it is doped with a charge carrier selected from Al, B, Ga, In and P. Such extrinsic semiconductor materials may be either of n-type in which negative charge carriers dominate or of p-type in which positive charge carriers dominate. Typical extrinsic p-type semiconductor material consists of silicon (Si) or germanium (Ge) doped with a charged carrier selected from aluminum (Al), Boron (B), Gallium (Ga) and indium (In); Typical extrinsic p-type semiconductor material consists of silicon (Si) or germanium (Ge) typically doped with phosphorus (P).

Nanoparticle Prepared from an Insulator Material Having a High Relative Dielectric Constant (Relative Permittivity), i.e. Equal to or Above 200

The nanoparticles prepared from, or consisting of, an insulator material having a band gap Eg equal to or above 3.0 eV, typically when measured at room temperature (25° C.) and a high relative dielectric constant $\varepsilon_{ijk}$ (also named relative permittivity), are typically prepared with a material having a relative dielectric constant $\varepsilon_{ijk}$ equal to or above 200, which is typically measured between 20° C. and 30° C. and between 10$^2$ Hz up to the infrared frequency (see for instance table 12-45 "Permittivity (dielectric constant) of inorganic solid"; Handbook of chemistry and physics; David R. Lide; 88$^{th}$ Edition; Compilation of the static dielectric constant of inorganic solid. K. F. Young and H. P. R. Frederikse. J. Phys. Chem. Ref Data, Vol. 2, No. 2, 1973).

Such nanoparticles are typically prepared with a dielectric material which is a mixed-metal oxide preferably selected from BaTiO$_3$, KTaNbO$_3$, KTaO$_3$, SrTiO$_3$, BaSrTiO$_3$, etc.

Nanoparticle Prepared from an Insulator Material Having a Low Relative Dielectric Constant (Relative Permittivity), i.e. Equal to or Below 100

The nanoparticles prepared from, or consisting of, an insulator material having a low relative dielectric constant are typically prepared with a material having a band gap Eg equal to or above 3.0 eV typically when measured at room temperature (25° C.) and a relative dielectric constant $\varepsilon_{ijk}$, equal to or below 100, preferably below 50 or below 20, which is typically measured between 20° C. and 30° C. and between 10$^2$ Hz up to the infrared frequency, (see for instance table 12-45 "Permittivity (dielectric constant) of inorganic solid"; Handbook of chemistry and physics; David R. Lide; 88$^{th}$ Edition; Compilation of the static dielectric constant of inorganic solid. K. F. Young and H. P. R. Frederikse. J. Phys. Chem. Ref Data, Vol. 2, No. 2, 1973).

Such nanoparticles are typically prepared with a dielectric material which is selected from a metal oxide, a mixed metal oxide, the metallic element of which is from period 3, 5 or 6 of the Mendeleev's periodic table or a lanthanide, and a carbon material. The dielectric material is preferably selected from Al$_2$O$_3$, LaAlO$_3$, La$_2$O$_3$, CeO$_2$, SiO$_2$, SnO$_2$, Ta$_2$O$_5$, ZrO$_2$, HfO$_2$, Y$_2$O$_3$ and carbon diamond.

The Nanoparticle's or Nanoparticles Aggregate's Shape

As the shape of the particle or aggregate can influence its "biocompatibility", particle or aggregate having a quite homogeneous shape is preferred. For pharmacokinetic reasons, nanoparticles or aggregates being essentially spherical, round or ovoid in shape are thus preferred. Such a shape also favors the nanoparticle's or aggregate's interaction with cells or uptake by cells. Spherical or round shape is particularly preferred.

The shape of the nanoparticle or aggregate of nanoparticles is typically evaluated using transmission electron microscopy (TEM).

The Nanoparticle's or Nanoparticles Aggregate's Dimension or Size

In the spirit of the invention, the terms "nanoparticle" or "nanoparticles' aggregate" refers to a product, in particular a synthetic product, with a size in the nanometer range, typically between 1 nm and 500 nm.

The term "aggregate of nanoparticles" or "nanoparticles' aggregate" refers to an assemblage of nanoparticles strongly, typically covalently, bound to each other.

Transmission electron microscopy (TEM) can be used to measure the size of the nanoparticle or of the aggregate of nanoparticles. As well, dynamic light scattering (DLS) can be used to measure the hydrodynamic diameter of nanoparticles or nanoparticles' aggregates in solution. These two methods may further be used one after each other to compare size measures and confirm said size. A preferred method is DLS (Ref. International Standard ISO22412 Particle Size Analysis-Dynamic Light Scattering, International Organisation for Standardisation (ISO) 2008), whereas the mean hydrodynamic diameter of the nanoparticle or the aggregate of nanoparticles in solution is given in intensity.

Typically, the largest dimension or size is the diameter of a nanoparticle of round or spherical shape, or the longest length of a nanoparticle of ovoid or oval shape.

The largest dimension of a nanoparticle or aggregate as herein defined is typically between about 2 nm and about 250 nm, preferably between about 4 nm or 10 nm and about 100 nm or about 200 nm, even more preferably between about 10 nm and about 150 nm.

The Nanoparticles' or Aggregates of Nanoparticles' Biocompatible Coating

In a preferred embodiment, the nanoparticle or nanoparticles' aggregate used in the context of the present invention to prepare a composition of interest can be coated with a biocompatible material selected from an agent exhibiting stealth property. Agent exhibiting stealth properties may be an agent displaying a steric group. Such a group may be selected for example from polyacrylate; polyacrylamide (poly(N-isopropylacrylamide)); polycarbamide; a biopolymer; a polysaccharide such as dextran or xylan; and collagen. In another preferred embodiment, the nanoparticles or nanoparticles' aggregates can be coated with a biocompatible material selected from an agent allowing interaction with a biological target. Such an agent can typically bring a positive or a negative charge on the nanoparticle's or nanoparticles' aggregate's surface. An agent forming a positive charge on the nanoparticle's or nanoparticles' aggregate's surface can be for example aminopropyltriethoxisilane or polylysine. An agent forming a negative charge on the nanoparticle's or nanoparticles' aggregate's surface can be for example a phosphate (for example a polyphosphate, a metaphosphate, a pyrophosphate, etc.), a carboxylate (for example citrate or dicarboxylic acid, in particular succinic acid) or a sulphate.

In a preferred embodiment, the nanoparticle or aggregate of nanoparticles used in the context of the present invention presents a hydrophilic neutral surface charge or is coated with a biocompatible material (i.e. a coating agent) selected from a hydrophilic agent conferring a neutral surface charge to the nanoparticle. Indeed, when the nanoparticles of the present invention are administered to a subject, nanoparticles presenting a hydrophilic neutral surface charge or nanoparticles coated with a biocompatible agent selected from a hydrophilic agent conferring a neutral surface charge to the nanoparticles are particularly advantageous to optimize the use of the herein described nanoparticles when exposed to an electrical stimulus/field.

A hydrophilic agent conferring neutral surface charge to the nanoparticle or nanoparticles' aggregate may be an agent displaying a functional group selected from an alcohol (R—OH), an aldehyde (R—COH), a ketone (R—CO—R), an ester (R—COOR), an acid (R—COOH), a thiol (R—SH), a saccharide (glucose, fructose, ribose for instance), an anhydride (RCOOOC—R), and a pyrrole. The hydrophilic agent conferring a neutral surface charge to the nanoparticle or nanoparticles' aggregate can be a monomer, a dimer, an oligomer, a polymer or a copolymer. When the agent is an oligomer, it may be an oligosaccharide such as a cyclodextrin. When the agent is a polymer, it may be a polyester (such as a poly(lactic acid) or a polyhydroxyalkanoic acid), a polyether, a polyethylene oxide, a polyethylene glycol, a polyvinylalcohol, a polycaprolactone, a polyvinylpyrrolidone, a polysaccharide such as a cellulose, a polypyrrole, etc.

In addition, a hydrophilic agent conferring neutral surface charge to the nanoparticle or nanoparticles' aggregate may be an agent displaying specific groups (R—) able to interact with the surface of the nanoparticle or aggregate of nanoparticles. R is typically selected from a thiol, a silane, a carboxylic and a phosphate group.

When the nanoparticle or aggregate of nanoparticles is a conductor or a semiconductor and a metallic nanoparticle, R is preferably a thiol, a thioether, a thioester, a dithiolane or a carboxylic group. Preferably, the hydrophilic neutral coating agent is selected from a thioglucose, a 2-mercaptoethanol, a 1-thioglycerol, a thiodiglycol and a hydroxybutyric acid.

When the nanoparticle or aggregate of nanoparticles is an insulator, and an oxide or a mixed-oxide nanoparticle, R is preferably a silane or a phosphate group. Preferably, the hydrophilic neutral coating agent is a hydroxymethyltriethoxysilane, a fructose 6-phosphate or a glucose 6-phosphate compound. A hydrophilic agent conferring neutral surface charge to the nanoparticle or nanoparticles' aggregate may be a zwitterionic compound such as an amino acid, a peptide, a polypeptide, a vitamin or a phospholipid.

The surface charge of a nanoparticle or nanoparticles' aggregate is typically determined, as well known by the skilled person, by zeta potential measurements, typically in water for a nanoparticles concentration between 0.2 and 10 g/L, for a pH between 6 and 8, and typically by adding electrolytes in water at concentrations between 0.001 and 0.2 M, for example 0.01 M or 0.15 M. Under the above defined conditions, the surface charge of the nanoparticle or aggregate of nanoparticles is typically comprised between −10 mV and +10 mV (corresponding to a neutral surface charge), between −20 mV and +20 mV, or between −35 mV and +35 mV.

A full biocompatible coating of the nanoparticle or aggregate may be advantageous in the context of the present invention in order to avoid any electrical charge on the nanoparticle's surface, when the nanoparticle presents a hydrophilic neutral surface charge. The "full coating" implies the presence of a very high density/compactness of biocompatible molecules able to create at least a complete monolayer on the surface of the particle.

The biocompatible coating allows in particular the nanoparticle's stability in a fluid, such as a physiological fluid (blood, plasma, serum, etc.) or any isotonic media or physiologic medium required for a pharmaceutical administration.

Stability may be confirmed by dry extract quantification using a drying oven and measured on a nanoparticle suspension prior and after filtration, typically on a 0.45 μm filter.

Advantageously, the coating preserves the integrity of the particle in vivo, ensures or improves the biocompatibility thereof, and facilitates an optional functionalization thereof (for example with spacer molecules, biocompatible polymers, targeting agents, proteins, etc.).

The biocompatible nanoparticle or aggregate of nanoparticles of the invention should neither dissolve and release toxic species following in vivo administration (i.e. at physiological pH) nor present redox behavior in absence of electrical stimulation.

Another particular object herein described relates to a composition, in particular a pharmaceutical composition, comprising nanoparticles and/or nanoparticles' aggregates such as defined hereinabove, preferably together with a pharmaceutically acceptable carrier or vehicle.

In particular, herein described is a composition for use in/for enhancing brain performances or for preventing or treating/for use in prevention or treatment of pathological stress or at least one symptom thereof as herein described in a subject exposed to an electric field, wherein the composition comprises, or consists of, nanoparticles and/or nanoparticles' aggregates and a pharmaceutically acceptable support, and wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100 as herein above explained.

In a preferred aspect, the composition comprises, or consists of, at least two distinct nanoparticles and/or nanoparticles' aggregates, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100.

The composition can be in the form of a solid, liquid (particles in suspension), aerosol, gel, paste, and the like. Preferred compositions are in a liquid or a gel form. Particularly preferred compositions are in liquid form.

The pharmaceutically acceptable support or carrier which is employed can be any classical support for the skilled person, such as for example a saline, isotonic, sterile, buffered solution, a non-aqueous vehicle solution and the like.

The composition can also comprise stabilizers, sweeteners, surfactants, polymers and the like.

It can be formulated for example as ampoule, aerosol, bottle, tablet, capsule, by using techniques of pharmaceutical formulation known by the skilled person.

The nanoparticles or nanoparticles' aggregates of the invention can be administered to the subject using different possible routes such as intra-cranial, intra venous (IV), airways (inhalation), intra-thecal, intra-ocular or oral route (per os), preferably using intra-cranial or intra-thecal.

Repeated injections or administrations of nanoparticles or nanoparticles' aggregates can be performed, when appropriate.

The herein described nanoparticles, nanoparticles' aggregates, and compositions comprising such nanoparticles or nanoparticles' aggregates are for use in a subject, typically for use in an animal, preferably in a mammal, even more preferably in a human being, whatever its age or sex.

Typical quantity(ies) of nanoparticles or aggregates of nanoparticles to be administered in the cerebral cortex, hippocampus or amygdala of the subject is(are) between $10^5$ and $10^{15}$, preferably between $10^7$ and $10^{14}$, more preferably between $10^9$ and $10^{12}$. Also typical quantity(ies) of nanoparticles or aggregates of nanoparticles to be administered in the cerebral cortex, hippocampus or amygdala of the subject is(are) between $10^2$ and $10^{12}$ nanoparticles or aggregates of nanoparticles per cm$^3$.

In the context of the invention, exposing nanoparticles or nanoparticles' aggregates to an electric field/stimulus is equivalent to exposing a subject, who has been administered with nanoparticles or nanoparticles' aggregates, to an electric field/stimulus.

Also herein described are a method for enhancing brain performances in a subject and a method for treating pathological stress or at least one symptom thereof in a subject, wherein each method comprises a step of administering anyone of the herein described nanoparticles or nanoparticles' aggregates to the subject and a step of exposing said subject to an electric field/stimulus.

A further object herein described relates to a kit comprising at least two distinct nanoparticles and/or nanoparticles' aggregates as herein described, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100 as herein described.

In a particular embodiment, the kit comprises, in distinct containers, distinct nanoparticles and/or nanoparticles aggregates as herein described (which are intended to be contacted, typically mixed, either in situ, i.e. on the target site, or in vitro or ex vivo before deposition of the mixture on the target site).

Also herein described is the use, in vivo, in vitro or ex vivo, of such a kit in a method as herein described for enhancing brain performances/capacities in a subject, typically for enhancing the effective connections in the neuronal network and thus the neuronal network's memory capacity in a subject, or in a method for preventing or treating pathological stress or at least one symptom thereof in a subject in need thereof. Also herein disclosed is a kit as herein described for use in prevention or treatment of pathological stress or of at least one symptom thereof in a subject.

The present invention aims in particular at enhancing brain performances thanks to the use of nanoparticles or nanoparticles' aggregates exposed to an electrical stimulus/field.

Figure 4:
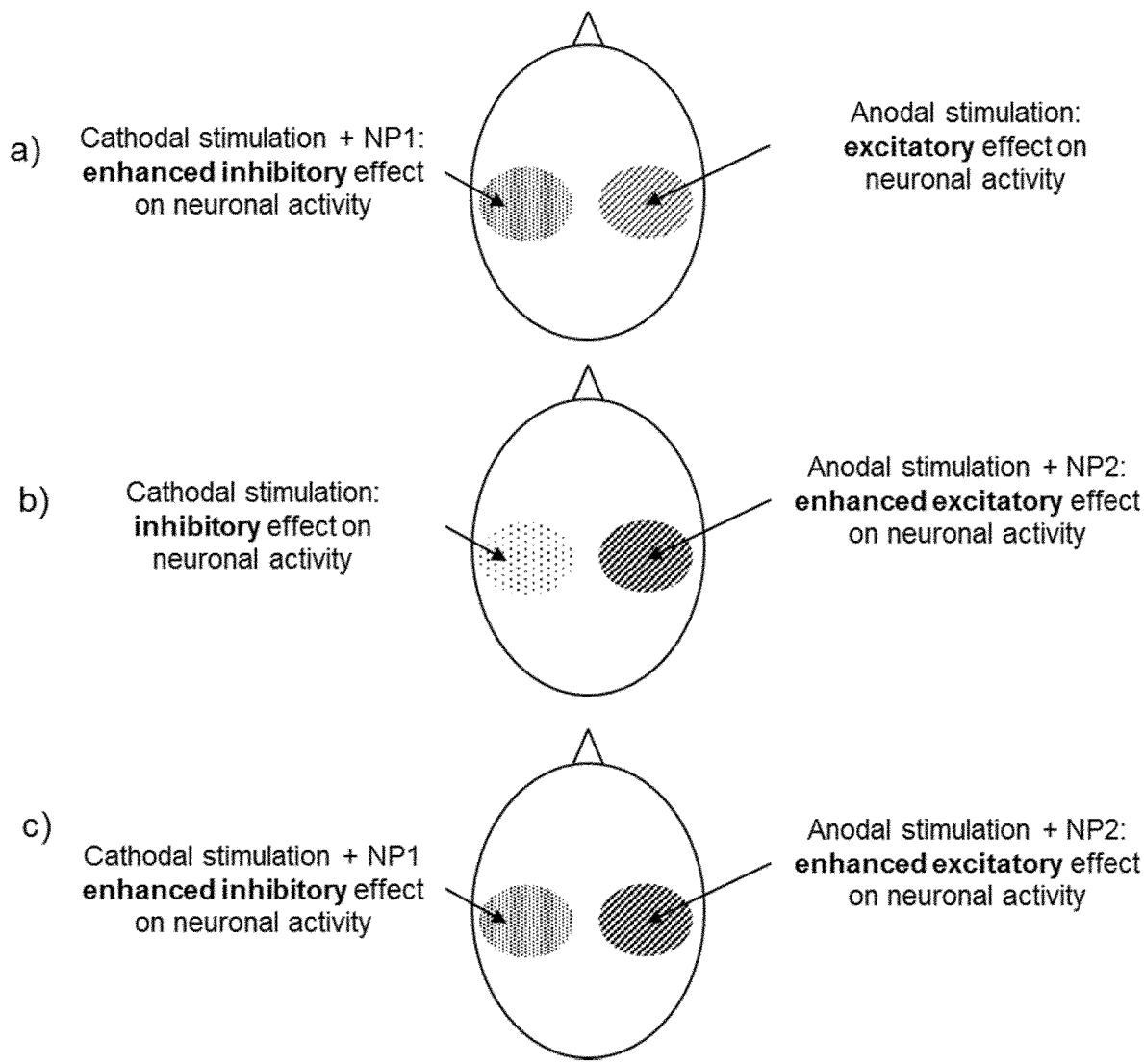

The nanoparticles or nanoparticles' aggregates of the present invention are, when exposed to an electrical stimulus/field, for use in/for enhancing brain performances/capacities, or for preventing or treating/for use in prevention or treatment of pathological stress or at least one symptom thereof in a subject in need of such a treatment, by increasing locally the inhibitory effect brought by a cathodal stimulation via the use of one type of nanoparticles "NP1" (i.e. insulating nanoparticles) and/or by increasing locally the excitatory effect brought by an anodal stimulation via the use of another type of nanoparticles "NP2" (i.e. conductor or semi-conductor nanoparticles) [cf. FIG. 4-a): local increase of inhibitory effect with nanoparticles "NP1", 4-b) local increase of excitatory effect with nanoparticles "NP2": 4-c): local increase of inhibitory effect with nanoparticles "NP1" and local increase of excitatory effect with nanoparticles "NP2"].

In a particular aspect, the nanoparticle or nanoparticles' aggregate herein described is for use, or for use in a method, in/for enhancing physical performances or in/for enhancing learning, memorizing, sense perception, attention and/or decision making of a subject in need of such a treatment.

In rodents, typically in mice, robust evidence of psychometric intelligence can be obtained from test batteries including different tasks. These tests typically include learning tasks such as odor discrimination or spatial navigation. A learning test is associated with a sensory, motor or motivational requirement imposed on the animal. For instance, to assess reasoning in mice, a test based on the concept of "fast mapping" (Carey S, et al., *Proceedings of the Standford Child Language Conference.*, 1978, 15, 17-29: *Acquiring a single new word*) can be used, to assess attentional task in mice, a "mouse Stroop test" may be used, and to assess the efficacy of working memory or working memory capacity in mice a "radial arm mazes" assay may be used (Matzel L. D et al. *Current Directions in Psychological Science*, 2013, 22(5), 342-348: *The architecture of intelligence. Converging evidence from studies of humans and animals*).

An IQ test may be used to assess memory capacity in the human being. IQ tests such as the Raven's Matrix or the Wechsler Adult Intelligence scale are well known by the skilled person and typically used to assess working memory capacity in the human being. The Stroop Color-Word Interference Test (Stroop J R, *Journal of Experimental Psychology*, 1935, 18, 643-652: *Studies of interference in serial verbal reactions*) may also be used in the human being to predict general intelligence (Huang L, et al., *Journal of Experimental Psychology: Human Perception and Performance*, 2012, 38, 414-428: *Measuring the interrelations among multiple paradigms of visual attention: an individual differences approach*).

In another particular aspect, the nanoparticle or nanoparticles' aggregate herein described is for preventing or treating/for use in prevention or treatment of a subject by enhancing neural/neurons connections, functional connectivity and/or synaptic plasticity in the brain of a subject in need of such a treatment.

In a typical aspect, the nanoparticle or nanoparticles' aggregate herein described is for preventing or treating/for use in prevention or treatment of a subject suffering of an altered brain functional activity.

In another particular aspect, the nanoparticle or nanoparticles' aggregate herein described is for preventing or treating/for use in prevention or treatment of a subject suffering from pathological stress or from at least one symptom thereof, in particular from chronic stress. All living organisms strive towards a dynamic equilibrium, which is called homeostasis. This equilibrium is threatened by certain physical and psychological events. The interface between the incoming sensory information and the appraisal process is formed by limbic brain structures, which include the hippocampus, the amygdala, and the prefrontal cortex. Various situations may trigger stress, such as novelty, uncertainty, frustration, conflict, fear, pain, etc. Constant exposure to adverse environment involving irritants such as noise, pollution, and interpersonal conflicts may also induce stress.

Pathological stress resulting from such cumulative and/or repetitive situations alters brain cells' structure (morphology) and/or connections and/or brain cells' functional properties. As a consequence, pathological stress severely affects health and limits the quality of human life.

Uncontrollable stress can have severe adverse repercussions and induces symptoms including deterioration in learning and memory capacity. At mild level of stress, certain neurochemical systems (for examples, catecholamines, glucocorticoids) might affect learning. As the level of stress increases (in duration and/or in intensity), several transient and permanent changes are observed in the hippocampus, including modifications in synaptic plasticity, cellular morphological changes, suppression of adult neurogenesis and/or neuronal destruction or atrophy (these changes are herein described as symptoms of pathological stress). These stress-associated changes in the brain influence learning-and-memory processes. Indeed, the hippocampus, amygdala and prefrontal cortex undergo stress-induced structural remodeling which alter behavioral and physiological responses. Chronic stress triggers atrophy of neurons in the hippocampus and prefrontal cortex, and in brain regions involved in memory, selective attention, and executive function, and causes hypertrophy of neurons in amygdala, a brain region involved in fear as well as aggressiveness. The ability to learn, remember and take decision can be compromised, and is typically decreased, by chronic stress, and may be accompanied by increased aggressiveness.

Extensive observations from in vitro and in vivo electrophysiological studies are consistent to show that stress and stress hormones impair Long Term Potentiation (LTP).

There are many pharmaceutical agents, such as sleeping drugs, anxiolytics and beta blockers that counter act some of the problems associated with being pathologically stressed out. Likewise, drugs that reduce oxidative stress or inflammation block cholesterol synthesis or absorption and treat insulin resistance or chronic pain can help dealing with the metabolic and neurological consequences of being "pathologically stressed out". All of these medications are valuable to some degree, yet unfortunately each one has its side effects and limitations (Kim J. J. et al. *Nature Reviews Neuroscience*, 2002, 3, 453-462: *The stressed hippocampus, synaptic plasticity and lost memories*; McEwen B. X. *Physiological Review*, 2007, 87, 873-904: *Physiology and neurobiology of stress and adaptation: central role of the brain*). The herein described nanoparticles can now advantageously be used to treat a subject suffering from such pathological stress, in particular from chronic stress, typically a subject having a brain in which stress-related changes as described herein above have been detected.

The term "Treatment" refers to therapeutic treatment or measures able to prevent, alleviate or cure a pathological stress or a symptom thereof as herein above described, in particular chronic stress. Such a treatment is intended for a mammal subject, preferably a human subject in need thereof. Are considered as such, the subjects already identified (diagnosed) as suffering from a pathological stress as herein described, or those considered "at risk of developing" such a pathological stress for whom the treatment is a preventive or prophylactic treatment. Particular subjects suffering from a pathological stress are the subjects who have been prescribed a drug selected from a sleeping drug, an anxiolytic and a beta blocker.

The examples which follow and their corresponding figures illustrate the invention without limiting the scope thereof.

FIGURES

FIG. 1. Modulation of the cortical excitability by tDCS: a) schema of a pyramidal cortical neuron; b) anodal stimulation; c) cathodal stimulation.

Figure 2:
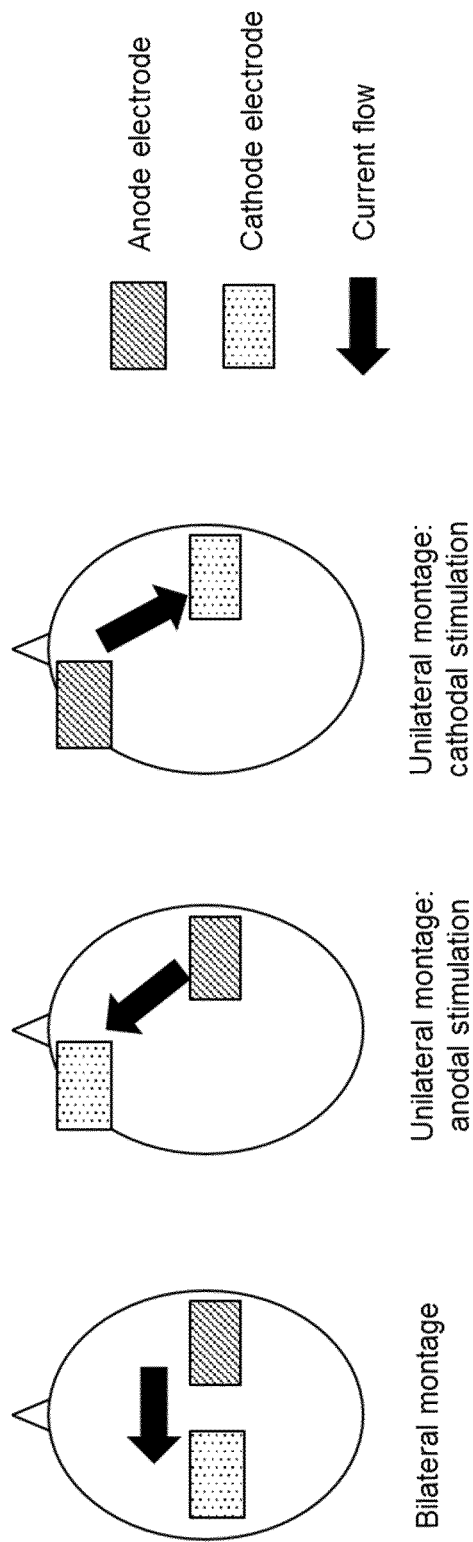

FIG. 2. Different electrodes montages for transcranial Direct Current Stimulation (tDCS).

Figure 3:
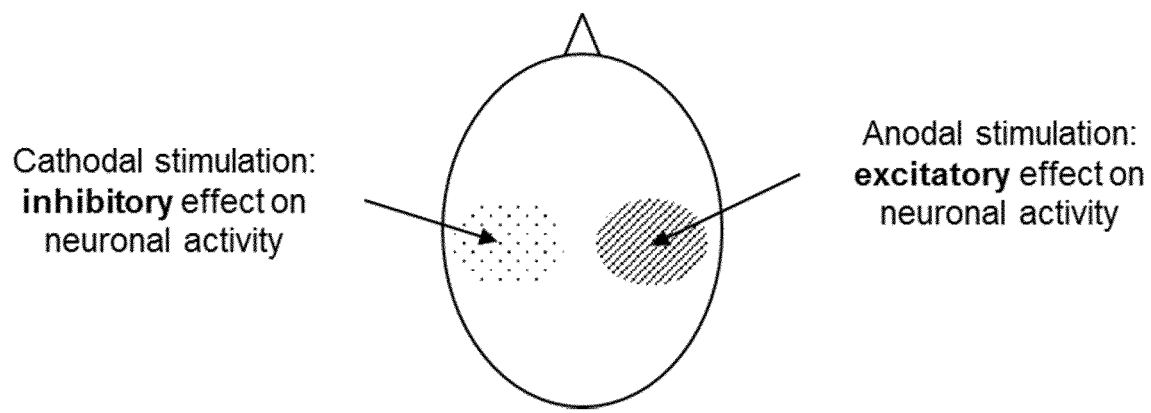

FIG. 3. Inhibitory and excitatory effects of electric stimulation (tDCS).

FIG. 4. a): local increase of inhibitory effect with nanoparticles "NP1", b) local increase of excitatory effect with nanoparticles "NP2", c): local increase of inhibitory effect with nanoparticles "NP1" and local increase of excitatory effect with nanoparticles "NP2"; where NP2 is a conductor or a semi-conductor and NP1 is an insulator.

Figure 5:
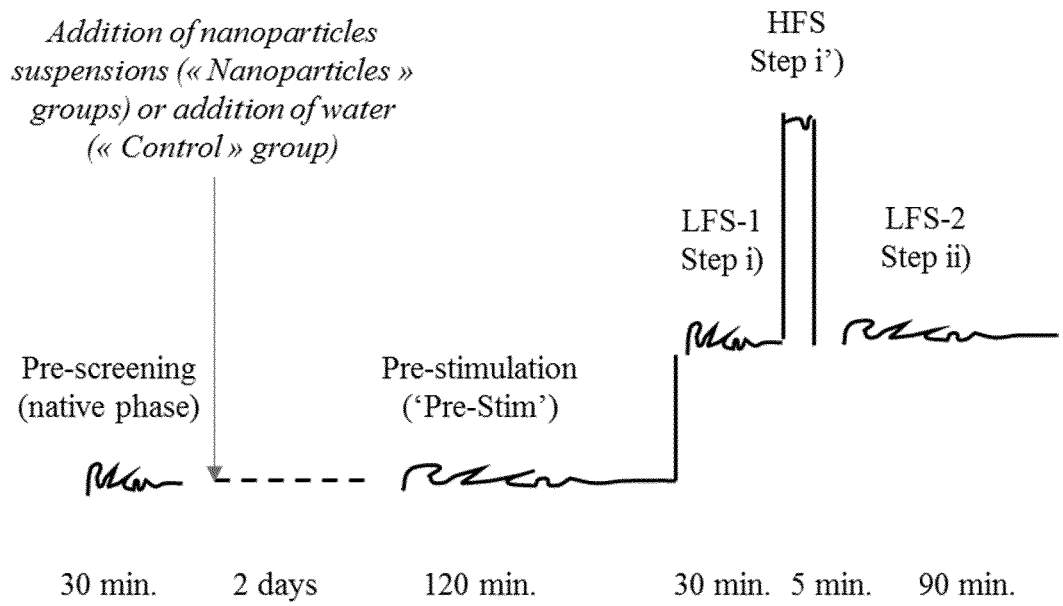

FIG. 5. Experimental scheme of the cultures of neurons exposed to low frequency stimulation (LFS) at step i) and step ii), with or without an intermediary step i') of high frequency stimulation (HFS). The mouse frontal cortex cultures were prepared from embryonic day 15/16 NMRI mice and cultured on 48 well MEAs for 26 days (culture period; native phase). The cultures were treated for 2 days with the suspensions of nanoparticles ("Nanoparticles" groups) or with water ("Control" group). After 2 days of incubation, the activity was recorded for 2 hours (term "Pre-Stim" recording). The recording was followed by two distinct steps (steps i) and ii)) or three distinct steps (steps i), i') and ii)) in the following order: a low frequency stimulation (LFS-1) phase for 30 minutes (step i)), optionally, an intermediary tetanic stimulation (high frequency, HFS) phase for 5 minutes (step i')), and a low frequency stimulation (LFS-2) phase for 90 minutes (step ii)). After the native phase, two active electrodes were identified per well and selected for stimulation. One of them was stimulated with LFS in steps i) and ii), and both electrodes were stimulated with HFS in step i') when carried out. Recording was performed during step i) (values were derived from 60 seconds bin data taken from a 30 minutes span) and step ii) (values were derived from 60 seconds bin data taken from a 30 minutes span after 60 minutes of LFS).

Figure 6:
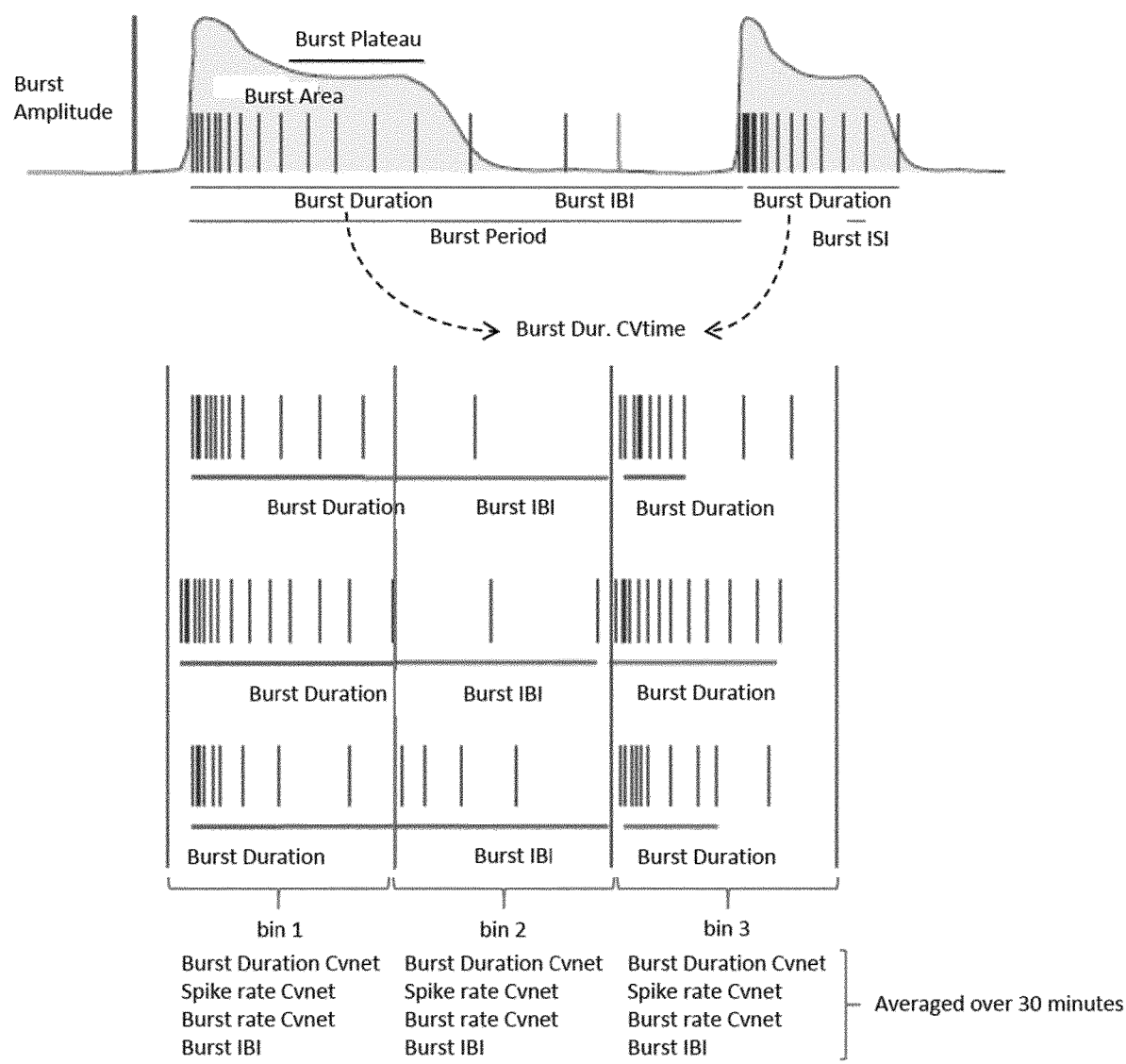

FIG. 6. Scheme of two simplified bursts outlining some of the parameters that can be extracted from the electrical activity recording. Parameters describing general activity (spike, burst, inter burst interval (IBI) and burst period) and burst structure (burst duration, burst plateau, burst amplitude, burst inter spike interval (ISI) and burst area) are indicated. Standard deviations (SD) of these parameters are measures for regularity of general activity and burst structure respectively. Coefficient of variation in time (CVtime) reflects the temporal regularity of the activity pattern of each unit. CVtime is calculated by the ratio of parameter's standard deviation and mean. Coefficient of variation among the network (CVnet) reflects synchronization among neurons within the network. CVnet is calculated by the ratio of parameter's standard deviation by mean over the network. Large CVnet values imply a wide range of variation in the activity across the network, meaning less synchronization.

Figure 7:
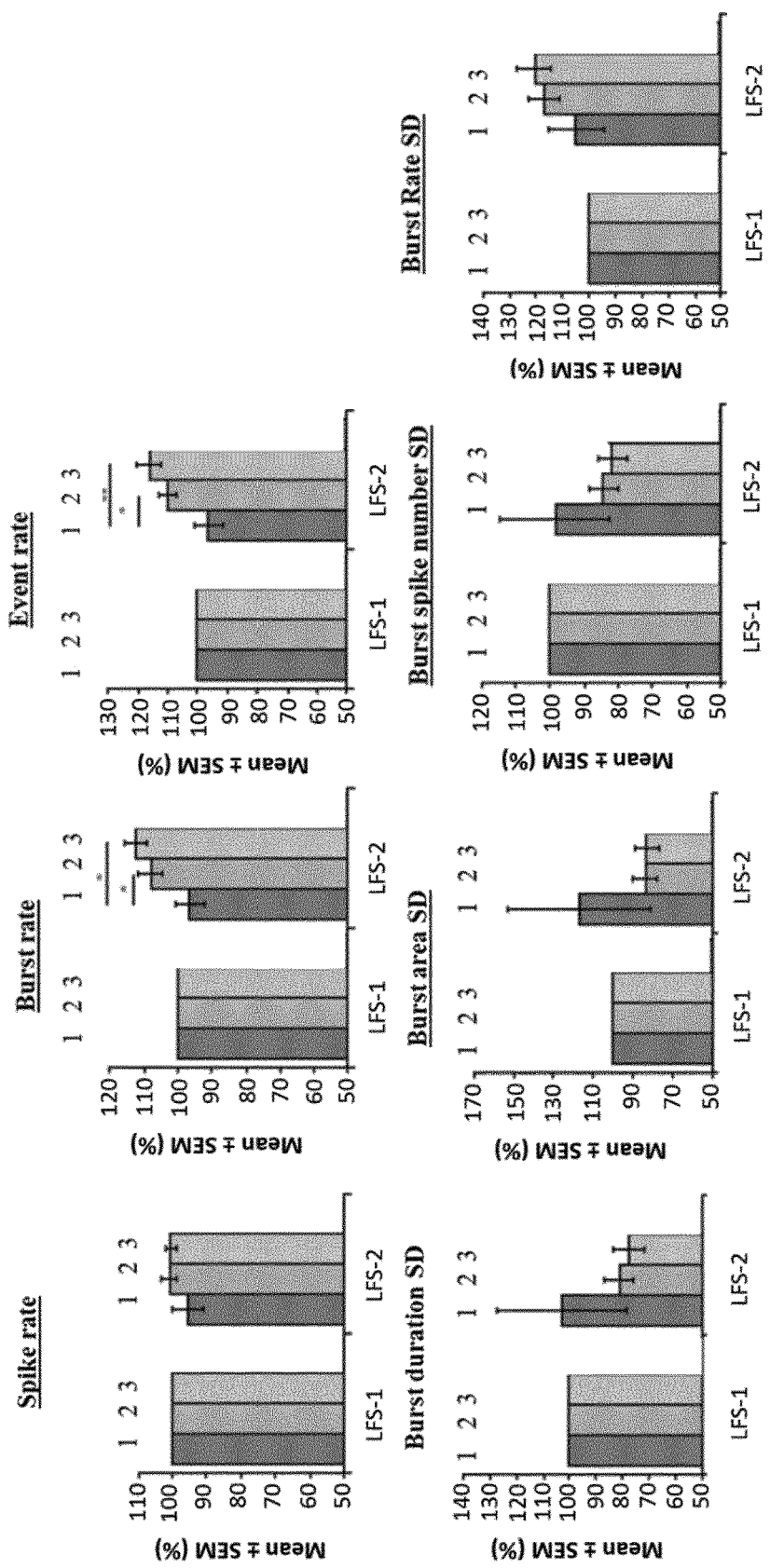

FIG. 7. Functional effects of "Nanoparticles" group (nanoparticles from example 3) when exposed to high frequency stimulation (HFS) compared to "Control" groups (no nanoparticles/with or without high frequency stimulation) on frontal cortex network activity. The results indicate HFS-specific potentiation at the cellular level in presence of nanoparticles when compared to "Control" groups.

Figure 8:
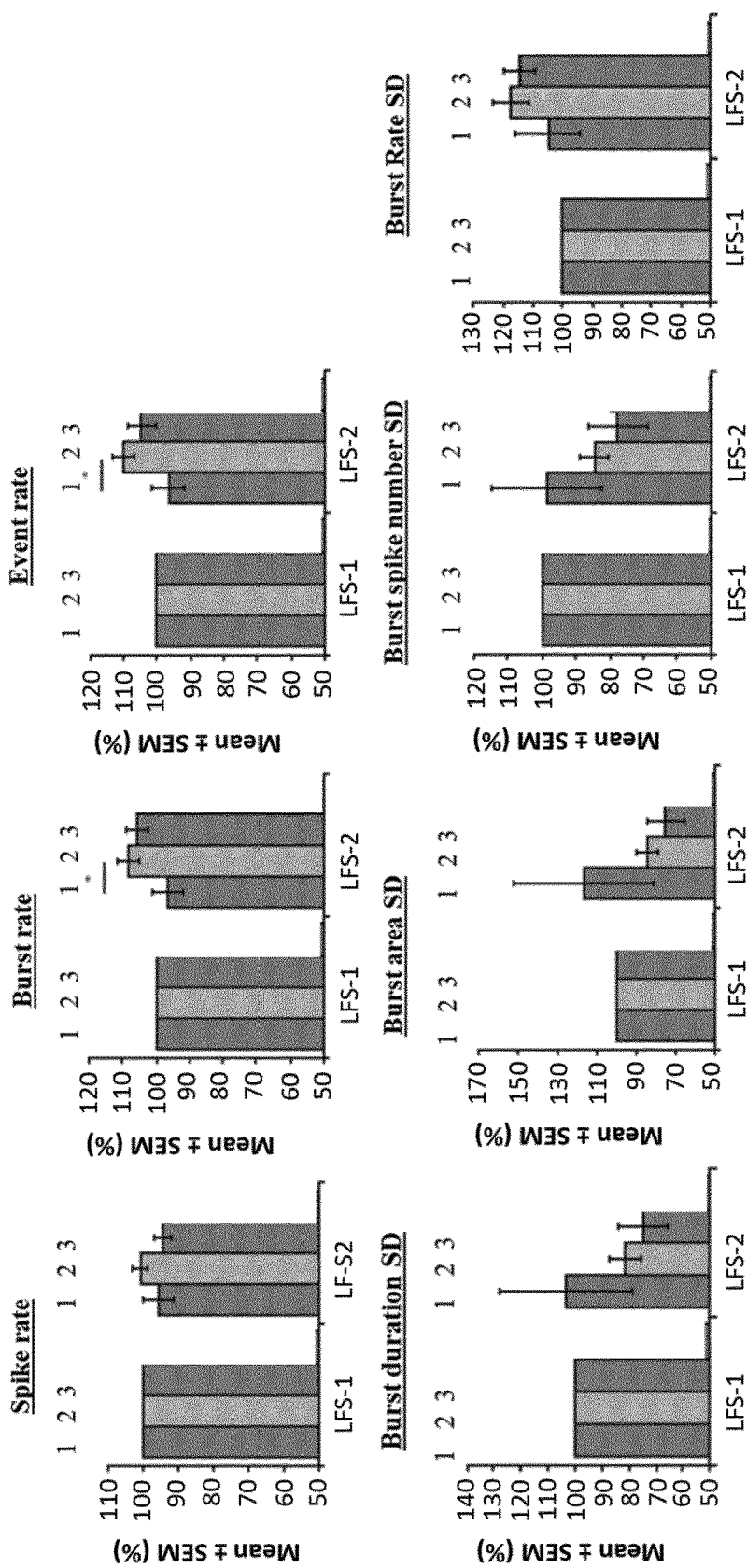

FIG. 8. Functional effects of "Nanoparticles" group (nanoparticles from example 1) when exposed to high frequency stimulation (HFS) compared to "Control" groups (with or without high frequency stimulation) on frontal cortex network activity. The results indicate HFS-specific potentiation at the cellular level in presence of nanoparticles when compared to "Control" groups.

EXAMPLES

Simulation

Simulation can be used to assess the effect on neuronal network(s) of nanoparticles exposed to an electrical stimulus (electric field).

In Vitro Studies of Neurons

At the neuron level, Patch clamp technique is very useful for detecting action potentials, as it allows simultaneous direct measurement and control of membrane potential of a neuron.

This technique is used to assess the effects of nanoparticles on a single neuron.

In Vitro Studies of a Network of Neurons

Multi-electrode arrays (MEAs) permit stimulation and recording of a large number of neurons (neuronal network). Dissociated neuronal cultures on MEAs provide a simplified model in which network activity can be manipulated with electrical stimulation sequences through the array's multiple electrodes. This technique is very useful to assess physiologically relevant questions at the network and cellular levels leading to a better understanding of brain function and dysfunction.

Dissociated neuronal cultures coupled to MEAs are indeed widely used to better understand the complexity of brain networks. In addition, the use of dissociated neuronal assemblies allows the manipulation and control of the network's connectivity. The use of dissociated neuronal cultures coupled to MEA allows the design of experiments where neurons can be extracellularly stimulated by mean of electrical pulses delivered through the same electrodes of the device. In this way, it becomes reasonable to investigate how the emerging neuronal dynamics can be modulated by the electrical stimulation, and, consequently, whether the underlying functional connectivity is modified or not (Poli D. et al, *Frontiers in Neural Circuits*, 2015, 9 (*article* 57), 1-14: *Functional connectivity in in vitro neuronal assemblies*).

The MEA system enables non-invasive, long-lasting, simultaneous extracellular recordings from multiple sites in the neuronal network in real time, increasing spatial resolution and thereby providing a robust measure of network activity. The simultaneous gathering of action potential and field potential data over long periods of time allows the monitoring of network functions that arise from the interaction of all cellular mechanisms responsible for spatiotemporal pattern generation (Johnstone A. F. M. et al., *Neurotoxicology* (2010), 31: 331-350, *Microelectrode arrays: a physiologically based neurotoxicity testing platform for the $21^{st}$ century*). Compared to patch-clamp and other single electrode recording techniques, MEA measures responses of a whole network, integrating global information on the interaction of all receptors, synapses and neuronal types which are present in the network (Novellino A. et al., *Frontiers in Neuroengineering.* (2011), 4(4), 1-14, *Development of micro-electrode array based tests for neurotoxicity: assessment of interlaboratory reproducibility with neuroactive chemicals*). As such, MEA recordings have been employed to understand neuronal communication, information encoding, propagation, and processing in neuronal cultures (Taketani, M., et al., (2006). *Advances in Network Electrophysiology*. New York, N.Y.: Springer; Obien et al., *Frontiers in Neurosciences*, 2015, 8(423): *Revealing neuronal functions through microelectrode array recordings*). The MEA technology is a sophisticated phenotypic high-content screening method to characterize functional changes in network activity in electrically active cell cultures which is very sensitive to neurogenesis, as well as to neurogenerative and neurodegenerative aspects. Moreover, neuronal networks grown on MEAs are known as being capable of responding to neuroactive or neurotoxic compounds in approximately the same concentration ranges that alter functions of an intact mammalian nervous system (Xia et al., *Alcohol*, 2003, 30, 167-174: *Histiotypic electrophysiological responses of cultured neuronal networks to ethanol*; Gramowski et al., *European Journal of Neuroscience*, 2006, 24, 455-465: *Functional screening of traditional antidepressants with primary cortical neuronal networks grown on multielectrode neurochips*; Gramowski et al., *Frontiers in Neurology*, 2015, 6(158): *Enhancement of cortical network activity in vitro and promotion of GABAergic neurogenesis by stimulation with an electromagnetic field with 150 MHz carrier wave pulsed with an alternating 10 and 16 Hz modulation*).

This technique is used to assess the effect of nanoparticles on neuronal network(s).

In Vivo Studies of a Network of Neurons

An appropriate animal model is considered to assess the effect on the neuronal networks of animals of nanoparticles of the invention when exposed to an electrical stimulus.

For instance, mazes are used to study spatial learning and memory in rats. Studies using a maze helps uncover general principles about learning that can be applied to many species, including humans. Today, mazes are typically used to determine whether different treatments or conditions affect learning and memory in rats.

Example 1. Nanoparticles Prepared with a Conductor Material: Synthesis of Gold Nanoparticles Coated with a Biocompatible Coating Having a Neutral Surface Charge Gold nanoparticles were synthesized by reducing a gold chloride salt ($HAuCl_4$) with a capping agent (sodium citrate) (protocol was adapted from G. Frens Nature Physical Science 241 (1973) 21). In a typical experiment, $HAuCl_4$ solution was heated to boiling. Subsequently, sodium citrate solution was added. The resulting solution was maintained under boiling for an additional period of 5 minutes.

A 0.22 μm filtration (filter membrane: poly(ether sulfone) (PES)) of the nanoparticles' suspension was performed and gold concentration in suspension was determined by a UV-visible spectroscopy assay at 530 nm.

A surface coating was performed using α-methoxy-ω-mercaptopoly(ethylene glycol) 20 kDa ("thiol-PEG20 kDa"). A sufficient amount of "thiol-PEG 20 kDa" was added to the nanoparticles' suspension to reach at least half a monolayer coverage (2.5 molecules/$nm^2$) on the gold nanoparticle surface. pH was adjusted between 7 and 7.2, and the nanoparticles' suspension was stirred overnight.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The hydrodynamic diameter of the so obtained biocompatible gold nanoparticles in suspension was found equal to 118 nm, with a polydispersity index (dispersion of the nanoparticles' population in size) of 0.13.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to −1 mV.

Example 2. Nanoparticles Prepared with a Conductor Material: Synthesis of Gold Nanoparticles Coated with a Biocompatible Coating Having a Negative Surface Charge Gold nanoparticles were prepared as described in example 1 (same gold inorganic core).

A 0.22 μm filtration on PES membrane filter was performed and gold concentration in suspension was determined by a UV-visible spectroscopy assay at 530 nm.

A biocompatible surface coating was performed using meso-2, 3-dimercaptosuccinic acid (DMSA). A sufficient amount of DMSA was added to the nanoparticles' suspension to reach at least half a monolayer coverage (2.5 molecules/$nm^2$) on the surface. pH was adjusted between 7 and 7.2, and the nanoparticles' suspension was stirred overnight.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The hydrodynamic diameter of the so obtained nanoparticles in suspension was equal to 76 nm, with a polydispersity index (dispersion of the nanoparticles' population in size) of 0.46.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to −23 mV.

Example 3. Nanoparticles Prepared with an Insulator Material Having a Low Relative Dielectric Constant Equal to or Below 100: Synthesis of Zirconium Oxide Nanoparticles Coated with a Biocompatible Coating Having a Neutral Surface Charge Zirconium oxide ($ZrO_2$) nanoparticles were synthesized by precipitation of zirconium chloride ($ZrCl_4$) with tetramethyl ammonium hydroxide (TMAOH) at a basic pH. The resulting suspension was transferred in an autoclave and heated at a temperature above 110° C. After cooling, the suspension was washed with deionized water and acidified.

A 0.22 μm filtration on PES membrane filter was performed and ($ZrO_2$) nanoparticles' concentration was determined by drying the aqueous solution into a powder and weighing the as-obtained mass.

A biocompatible coating was prepared using silane-poly (ethylene) glycol 2 kDa ("Si-PEG 2 kDa"). A sufficient amount of "Si-PEG 2 kDa" was added to the nanoparticles' suspension to reach at least half a monolayer coverage (2.5 molecules/$nm^2$) on the surface. The nanoparticles' suspension was stirred overnight and subsequently the pH was adjusted to 7.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The nanoparticles' hydrodynamic diameter was found equal to 55 nm, with a polydispersity index (dispersion of the nanoparticles' population in size) of 0.1.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH7 was found equal to −1 mV.

Example 4. Nanoparticles Prepared with an Insulator Material Having a Low Relative Dielectric Constant Equal to or Below 100: Synthesis of Zirconium Oxide Nanoparticles Coated with a Biocompatible Coating Having a Negative Surface Charge Zirconium oxide nanoparticles were prepared as described in example 3 (same inorganic core).

A 0.22 μm filtration on PES membrane filter was performed and the ($ZrO_2$) nanoparticles' concentration was determined by drying the aqueous suspension to a powder and weighing the as-obtained mass.

Surface functionalization was performed using sodium hexametaphosphate. A sufficient mass of sodium hexametaphosphate was added to the nanoparticles' suspension to reach at least half a monolayer coverage (2.5 molecules/$nm^2$) on the surface. The nanoparticles' suspension was stirred overnight and pH was subsequently adjusted to 7.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The nanoparticles' hydrodynamic diameter was found equal to 70 nm, with a polydispersity index (dispersion of the nanoparticles population in size) of 0.11.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to −33 mV.

Example 5. Nanoparticles Prepared with a Semiconductor Material: Silicon Nanoparticles Coated with a Biocompatible Coating Having a Negative Surface Charge Silicon (Si) nanoparticles (powder) were obtained from US Research Nanomaterials Inc. They were dispersed in water at 30 g/L under sonication (with a probe).

A 0.22 µm filtration on PES membrane filter was performed and the (Si) nanoparticles' concentration was determined by drying the suspension to a powder and weighing the as-obtained mass.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The nanoparticles' hydrodynamic diameter was found equal to 164 nm, with a polydispersity index (dispersion of the nanoparticles' population in size) of 0.16.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH7 was found equal to −19 mV.

Example 6. Nanoparticles Prepared with an Insulator Material Having a High Relative Dielectric Constant Equal to or Above 200: Barium Titanate Nanoparticles Coated with a Biocompatible Coating Having a Negative Surface Charge Barium titanate ($BaTiO_3$) nanoparticles' suspension (20% wt in water) was obtained from US Research Materials Inc. (US3835).

Surface functionalization was performed using Silane-poly(ethylene) glycol 10 kDa ("Si-PEG 10 kDa"). Briefly, "Si-PEG 10 kDa" was first dissolved in an ethanol/water solution (1/3 v/v) and added to the $BaTiO_3$ suspension (20% wt in water) to achieve a full monolayer coverage on the surface of the nanoparticles. The suspension was sonicated and subsequently stirred overnight. After a 0.22 µm filtration (filter membrane: poly(ether sulfone)), a washing step was performed in order to eliminate unreacted "Si-PEG 10 kDa" polymers.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The nanoparticles' hydrodynamic diameter was found equal to 164 nm, with a polydispersity index (dispersion of the nanoparticles' population in size) of 0.16.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH7 was found at −11 mV.

Example 7. Long Term Plasticity Study Using Electrical Stimulation of Frontal Cortex Neurons with MEAs and Functional Evaluation of the Nanoparticles of the Invention Material and Methods
Microelectrode Array Neurochips The 48 well microelectrode array neurochips were purchased from Axion Biosystems Inc. These chips have 16 passive electrodes per well. The surface was coated for 1 hour with Polyethyleneimine (PEI, 50% in Borate buffer), washed and air-dried.

Primary Cell Culture, Treatment Conditions and Electrical Stimulation

Frontal cortex tissue was harvested from embryonic day 15/16 chr:NMRI mice (Charles River). Mice were sacrificed by cervical dislocation. Tissue was dissociated by enzymatic digestion (133.3 Kunitz units/ml DNase; 10 Units/ml Papain) and mechanical trituration, counted, vitality controlled, and plated in a 20 µl drop of DMEM containing laminin (10 µg/ml), 10% fetal bovine serum and 10% horse serum on MEAs. Cultures on MEAs were incubated at 37° C. in a 10% $CO_2$ atmosphere until ready for use. The developing co-cultures were treated with the mitosis inhibitors 5-fluoro-2'-deoxyuridine (25 µM) and uridine (63 µM) on day 5 after seeding to prevent further glial proliferation. Culture media were replenished two times a week with DMEM containing 10% horse serum.

The frontal cortex was cultured for 26 days (culture period, also identified as "native phase"). The number of active wells was quantified and the nanoparticles' suspensions (800 µM) ("Nanoparticles" groups) or water ("Control" group) were added to the active wells. After 2 days (48 hours) of incubation, the activity was recorded for 2 hours ("Pre-Stim" recording), followed by 30 minutes of low frequency stimulation (LFS-1) (step i)), and 90 minutes of low frequency stimulation (LFS-2) (step ii)), with or without an intermediary step i') (after step i) and before step ii)) of tetanic stimulation (high frequency, HFS) for 5 minutes. After the native phase, two active electrodes were identified per well and selected for stimulation. One of them was stimulated with LFS in steps i) and ii), and both electrodes were stimulated with HFS in step i'). Recording was performed in step i) (values were derived from 60 seconds bin data taken from a 30 minutes span) and ii) (values were derived from 60 seconds bin data taken from a 30 minutes span after 60 minutes of LFS) (cf. FIG. 5).

Electrical Stimulation Parameters
Low Frequency Stimulation (steps i) and ii)): 30 minutes or 90 minutes
Stimulation of one electrode per well in 48 well MEA
Minimum stimulation duration: 100 µs
Artefact elimination of 2 ms after pulse
1 pulse (biphasic) at +/−500 mV (frequency 0.2 Hz)
High Frequency Stimulation (step i')): 5 minutes
Stimulation of one electrode per well in 48 well MEA
Minimum stimulation duration: 100 µs
Artefact elimination of 2 ms after pulse 11 pulses (biphasic) at +/−500 mV (frequency 20 Hz) and a pulse trains period (frequency 0.2 Hz)

Multichannel Recording and Multiparametric Data Analysis

For the recording, the multichannel MAESTRO recording system by Axion Biosystems (USA) was used. For extracellular recording, 48-well MEAs were placed into the MAESTRO recording station and maintained at 37° C. Recordings were made in DMEM/10% heat inactivated horse serum. The pH was maintained at 7.4 with a continuous stream of filtered, humidified airflow with 10% $CO_2$.

Each unit represents the activity originating from one neuron recorded at one electrode. Units are separated at the beginning of the recording. For each unit, action potentials (i.e. spikes), were recorded as spike trains, which are clustered in so-called "bursts". Bursts were quantitatively described via direct spike train analysis using the programs Spike Wrangler and NPWaveX (both NeuroProof GmbH, Rostock, Germany). Bursts were defined by the beginning and end of short spike events (cf. FIG. 6).

With a multiparametric high-content analysis of the network activity patterns, 204 activity-describing spike train parameters were extracted. These parameters allow obtaining a precise description of activity changes in the following four categories: general activity, burst structure, oscillatory behavior and synchronicity.

- Changes in "general activity parameters" describe the effects on action potential firing rate (spike rate), burst rate, and burst period as the time between the bursts.
- "Burst structure parameters" define not only the internal structure of spikes within a high-frequency spiking phase ("burst"), e.g., spike frequency in bursts, spike rate in bursts, and burst spike density, but also the overall structure of the burst, such as duration, area, and plateau.
- "Oscillatory parameters" quantify the regularity of occurrence or structure of bursts, which is calculated by coefficients of variation of primary activity parameters describing the variability of parameters (general activity, burst structure) within experimental episodes (Gramowski A. et al., *Eur. J. Neurosci.*, 2004, 19, 2815-2825: *Substance identification by quantitative characterization of oscillator activity in murine spinal cord networks on microelectrode arrays*). Higher values indicate less regular burst structure or less regular general activity (e.g., spiking, bursting).
- As a measure of synchronicity in the spike trains, "CVnet parameters" reflect "synchronization" among neurons within the network (Gramowski A. et al., *Eur. J. Neurosci.*, 2004, 19, 2815-2825: *Substance identification by quantitative characterization of oscillator activity in murine spinal cord networks on microelectrode arrays*). CVnet is the coefficient of variation over the network. Large CVnet values imply a wide range of variation in the activity across the network, meaning less synchronization. (Gramowski A. et al., *Frontiers in Neurology*, 2015, 6(158): *Enhancement of cortical network activity in vitro and promotion of GABAergic neurogenesis by stimulation with an electromagnetic field with 150 MHz carrier wave pulsed with an alternating 10 and 16 Hz modulation*).

Functional effects induced by high frequency stimulation (HFS) on neuronal network, in the presence or in the absence of the nanoparticles of the invention, were evaluated through the above described parameters (also recapitulated for some of them in Table 1 below).

TABLE 1

Activity-describing parameters from the multiparametric data analysis in the two following categories: general activity and oscillatory behavior.

| | | |
|---|---|---|
| General activity | Spike rate | Number of spikes per second, averaged over all spike trains recorded |
| | Burst rate | Number of bursts per minute, averaged over all units recorded |
| | Event rate | Number of events per minute. Event is defined as synchronous burst activity of at least 50% of all units in a network within a time frame of 300 ms |
| Oscillatory behavior | Burst duration SD | Standard deviation of burst duration, reflecting the variability of burst duration within experimental episodes |
| | Burst area SD | Standard deviation of area under the curve after integrating the burst, defined by burst duration, number of spikes in bursts, spike frequency in bursts. The parameter describes the variability of burst area within experimental episodes. Higher values indicate less regular burst structure. |
| | Burst spike number SD | Standard deviation of spike number in bursts describes the variation of single unit spike number in burst within experimental episodes. Lower values are a measure for lower degree of variation in burst spike number, therewith a more regular burst structure. |
| | Burst rate SD | Standard deviation of number of bursts per minute, indicating the variability of burstiness of units within experimental episodes. |

Functional effects on network activity during LFS-2 (step ii), therefore after the HFS step i'), in the presence of the tested nanoparticles or in the absence thereof, were normalized to the "LFS-1" activity, i.e. the activity measured during low frequency stimulation step i). Values were derived from 60 seconds bin data taken from a 30 minutes span. Results (parameter values) were expressed as mean±SEM of independent networks. For each "Nanoparticles" group or "Control" group, at least 8 active wells ("active" meaning wells with a sufficient number of electrodes measuring electrical activity) were included in the analysis. The absolute parameters' distributions were tested for normality and the statistical significance between groups was assessed via one-way ANOVA.

FIGS. 7 and 8 present some representative parameters (general activity and oscillatory behavior) characterizing functional effects induced by HFS for the "Control" groups and for the "Nanoparticles" groups (nanoparticles from example 1 and from example 3). An increase of these effects beyond the "Control" groups' effects in the presence of nanoparticles at the cellular level, indicates a potentiating effect due to these nanoparticles.

FIG. 7 shows that pretreatment of the neuronal network with nanoparticles from example 3 and exposition to high frequency electrical stimulation (HSF) increases functional effects when compared to the "Control" groups. Interestingly, enhanced functional effects are observed for parameters belonging to the general activity category (typically "burst rate" and "event rate"), and they reach levels beyond that observed in the HFS-stimulated "Control" group. This indicates a nanoparticle-specific HFS-mediated potentiation which can be correlated to an enhancement of effective connections in the network and thus to an enhancement of the neuronal network's memory capacity. FIG. 8 shows that pretreatment of the neuronal network with nanoparticles from example 1 and exposition to high frequency electrical stimulation (HSF) increase functional effects when compared to the "Control" groups. Interestingly, enhanced functional effects are observed for parameters belonging to the oscillatory behavior category (typically "burst duration SD", "burst area SD" and "burst spike number SD"), and they reach more favorable levels than that observed in HFS-stimulated "Control" group. This indicates a nanoparticle-specific HFS-mediated potentiation which can be correlated to restructured bursts facilitating information storage within the network and thus enhancing the neuronal network's memory capacity.

These results highlight the advantageous performances of the nanoparticles described in the present application in enhancing functional effects (neurons connection and information storage within the neuronal network) induced by an electrical stimulation in the neuronal network.

The invention claimed is:

1. A method for enhancing learning, memorizing, sense perception, attention and/or decision making or treating chronic stress in a subject, wherein the method comprises i) administering a nanoparticle or nanoparticle aggregate to the subject, the nanoparticle or nanoparticle aggregate material being selected from a metal having a standard reduction potential E° above 0.2 that is Ir, Pd, Pt, Au, or a mixture thereof, an insulator material with a dielectric constant $\varepsilon_{ijk}$ equal to or above 200, and an insulator material with a dielectric constant $\varepsilon_{ijk}$ equal to or above 100, and wherein the nanoparticle and/or nanoparticle aggregate are coated with a biocompatible agent conferring a neutral surface charge, or with a biocompatible agent conferring a negative surface charge, and ii) exposing the nanoparticle or nanoparticle aggregate to an electric field applied through transcranial electric stimulation or transcranial magnetic stimulation.

2. The method according to claim 1, wherein the material is an insulator material with a band gap Eg equal to or above 3.0 eV and the relative dielectric constant $\varepsilon_{ijk}$ is measured between 20° C. and 30° C. and between $10^2$ Hz up to the infrared frequency.

3. The method according to claim 2, wherein the material is an insulator material with a band gap Eg equal to or above 3.0 eV and the relative dielectric constant $\varepsilon_{ijk}$ is equal to or above 200 and the material of the nanoparticle or nanoparticle aggregate is a dielectric material which is a mixed-metal oxide selected from $BaTiO_3$, $KTaNbO_3$, $KTaO_3$, $SrTiO_3$ and $BaSrTiO_3$.

4. The method according to claim 2, wherein the material is an insulator material with a band gap Eg equal to or above 3.0 eV and the relative dielectric constant $\varepsilon_{ijk}$ is equal to or above 100 and the material of the nanoparticle or nanoparticle aggregate is a dielectric material which is selected from a metal oxide, a mixed metal oxide, the metallic element of which is from period 3, 5 or 6 of the Mendeleev periodic table or a lanthanide, and a carbon material.

5. The method according to claim 1, wherein the nanoparticle or nanoparticle aggregate material is an insulator material with a dielectric constant $\varepsilon_{ijk}$ equal to or below 100 and is selected from $Al_2O_3$, $LaAlO_3$, $La_2O_3$, $CeO_2$, $SiO_2$, $SnO_2$, $Ta_2O_5$, $ZrO_2$, $HfO_2$ and $Y_2O_3$.

6. The method according to claim 5, wherein the nanoparticle or nanoparticle aggregate material is the insulator material with a dielectric constant $\varepsilon_{ijk}$ equal to or below 100 is selected from $ZrO_2$ and $HfO_2$.

7. The method according to claim 1, wherein the biocompatible agent conferring a neutral surface charge is a hydrophilic agent displaying a functional group selected from an alcohol (R—OH), an aldehyde (RCOH), a ketone (R—CO—R), an ester (R—COOR), an acid (R—COOH), a thiol (R—SH), a saccharide, glucose, fructose, ribose, an anhydride (RCOOOC—R), and a pyrrole.

8. The method according to claim 7, wherein R is selected from a thiol, a silane, a carboxylic and a phosphate group.

9. The method according to claim 1, wherein the biocompatible agent conferring a neutral surface charge to the nanoparticle or nanoparticle aggregate is hydrophilic agent that is a monomer, a dimer, an oligomer, a polymer or a copolymer.

10. The method according to claim 9, wherein the oligomer is an oligosaccharide.

11. The method according to claim 10, wherein the oligosaccharide is cyclodextrin.

12. The method according to claim 9, wherein the polymer is selected from a polyester, a polyether, a polyethylene oxide, a polyethylene glycol, a polyvinylalcohol, a polycaprolactone, a polyvinylpyrrolidone, a polysaccharide and a polypyrrole.

13. The method according to claim 12, wherein the polyester is a poly(lactic acid) or a polyhydroxyalkanoic acid.

14. The method according to claim 12, wherein the polysaccharide is cellulose.

15. The method according to claim 1, wherein the biocompatible agent conferring a negative surface charge is a phosphate or a sulphate.

16. The method according to claim 15, wherein the biocompatible agent conferring a negative surface charge is selected from a polyphosphate, a metaphosphate and a pyrophosphate.

17. A method for enhancing learning, memorizing, sense perception, attention and/or decision making or treating chronic stress in a subject, wherein the method comprises i) administering a composition to the subject, the composition comprising nanoparticles and/or nanoparticle aggregates and a pharmaceutically acceptable support, and the nanoparticle or nanoparticle aggregate material being selected from a metal having a standard reduction potential E° above 0.2 that is Ir, Pd, Pt, Au, or a mixture thereof, an insulator material with a dielectric constant $\varepsilon_{ijk}$ equal to or above 200, and an insulator material with a dielectric constant $\varepsilon_{ijk}$ equal to or below 100, and wherein the nanoparticle and/or nanoparticle aggregate are coated with a biocompatible agent conferring a neutral surface charge, or with a biocompatible agent conferring a negative surface charge, and ii) exposing the subject to an electric field applied through transcranial electric stimulation or transcranial magnetic stimulation.

18. The method according to claim 17, wherein the composition comprises at least two distinct nanoparticles and/or nanoparticle aggregates.

19. The method according to claim 17, wherein the nanoparticle or nanoparticle aggregate material is an insulator material with a dielectric constant $\varepsilon_{ijk}$ equal to or below 100 and is selected from $Al_2O_3$, $LaAlO_3$, $La_2O_3$, $CeO_2$, $SiO_2$, $SnO_2$, $Ta_2O_5$, $ZrO_2$, $HfO_2$ and $Y_2O_3$.

20. The method according to claim 19, wherein the nanoparticle or nanoparticle aggregate material is the insulator material with a dielectric constant $\varepsilon_{ijk}$ equal to or below 100 is $ZrO_2$ or $HfO_2$.

21. A kit comprising at least two distinct nanoparticles and/or nanoparticle aggregates, each nanoparticle or nanoparticle aggregate comprising a distinct material selected from a metal having a standard reduction potential E° above 0.2 that is Ir, Pd, Pt, Au, or a mixture thereof, an insulator material with a dielectric constant $\varepsilon_{ijk}$ equal to or above 200 and an insulator material with a dielectric constant $\varepsilon_{ijk}$ equal to or below 100, and wherein the nanoparticle and/or nanoparticle aggregate are coated with a biocompatible agent conferring a neutral surface charge, or with a biocompatible agent conferring a negative surface charge.

* * * * *